(12) United States Patent
Yamaguchi et al.

(10) Patent No.: US 11,103,464 B2
(45) Date of Patent: Aug. 31, 2021

(54) AQUEOUS COMPOSITION FOR OPHTHALMOLOGICAL USE OR OTOLARYNGOLOGICAL USE

(71) Applicant: ROHTO PHARMACEUTICAL CO., LTD., Osaka (JP)

(72) Inventors: Satoshi Yamaguchi, Osaka (JP); Kazuhiro Tsuji, Osaka (JP)

(73) Assignee: Rohto Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 15/038,897

(22) PCT Filed: Nov. 28, 2014

(86) PCT No.: PCT/JP2014/081551
§ 371 (c)(1),
(2) Date: May 24, 2016

(87) PCT Pub. No.: WO2015/080249
PCT Pub. Date: Jun. 4, 2015

(65) Prior Publication Data
US 2017/0027880 A1    Feb. 2, 2017

(30) Foreign Application Priority Data

Nov. 29, 2013   (JP) ............................ JP2013-248029

(51) Int. Cl.
| | | |
|---|---|---|
| *A61K 31/01* | (2006.01) | |
| *A61K 31/355* | (2006.01) | |
| *A61K 47/02* | (2006.01) | |
| *A61K 47/10* | (2017.01) | |
| *A61K 47/18* | (2017.01) | |
| *A61K 47/26* | (2006.01) | |
| *A61K 47/44* | (2017.01) | |
| *A61K 9/00* | (2006.01) | |
| *A61K 9/08* | (2006.01) | |
| *A61K 36/18* | (2006.01) | |
| *A61K 9/12* | (2006.01) | |
| *A61K 9/107* | (2006.01) | |

(52) U.S. Cl.
CPC ............ *A61K 31/01* (2013.01); *A61K 9/0043* (2013.01); *A61K 9/0048* (2013.01); *A61K 9/08* (2013.01); *A61K 9/107* (2013.01); *A61K 9/12* (2013.01); *A61K 31/355* (2013.01); *A61K 36/18* (2013.01); *A61K 47/02* (2013.01); *A61K 47/10* (2013.01); *A61K 47/26* (2013.01); *A61K 47/44* (2013.01)

(58) Field of Classification Search
CPC .... A61K 31/01; A61K 9/0043; A61K 9/0048; A61K 9/08; A61K 9/107; A61K 9/12; A61K 31/355; A61K 36/18; A61K 47/10; A61K 47/02; A61K 47/183; A61K 47/26; A61K 47/44
See application file for complete search history.

(56) References Cited

U.S. PATENT DOCUMENTS

| | | | | |
|---|---|---|---|---|
| 2011/0136912 A1* | 6/2011 | Ketelson | ................ | A61K 9/107 514/642 |
| 2011/0152307 A1* | 6/2011 | Babiole Saunier | .. | A61K 9/0048 514/291 |
| 2013/0296446 A1* | 11/2013 | Furumiya | ................ | A61K 9/08 514/783 |
| 2014/0302146 A1* | 10/2014 | Kurose | .................. | A61K 47/10 424/489 |

FOREIGN PATENT DOCUMENTS

| | | | | |
|---|---|---|---|---|
| CN | 101332183 A | 12/2008 | | |
| CN | 102764230 A | 11/2012 | | |
| JP | 2010-120856 A | 6/2010 | | |
| JP | 2011-093889 A | 5/2011 | | |
| JP | 2011-246418 A | 12/2011 | | |
| JP | WO 2013008714 A1 * | 1/2013 | ............. | A61K 47/10 |
| WO | WO-2012090985 A1 * | 7/2012 | ............... | A61K 9/08 |

OTHER PUBLICATIONS

Cosmetics Info., "Petrolatum". Retrieved Nov. 9, 2017. Retrieved from the internet <URL: http://www.cosmeticsinfo.org/ingredient/petrolatum-0>; pp. 1-3.*
International Search Report issued in corresponding International Patent Application No. PCT/JP2014/081551 dated Mar. 3, 2015.
International Preliminary Report on Patentability and Written Opinion issued in corresponding International Patent Application No. PCT/JP2014/081551 dated Jun. 9, 2016.

* cited by examiner

*Primary Examiner* — Doan T Phan
(74) *Attorney, Agent, or Firm* — Morgan, Lewis & Bockius LLP

(57) ABSTRACT

The present invention relates to an aqueous composition for ophthalmological use or otolaryngological use, the aqueous composition containing: (A) a petrolatum; and two or more (B) nonionic surfactants.

12 Claims, 2 Drawing Sheets

REFERENCE EXAMPLE 1 REFERENCE EXAMPLE 2

AQUEOUS COMPOSITION FOR OPHTHALMOLOGICAL USE OR OTOLARYNGOLOGICAL USE

TECHNICAL FIELD

The present invention relates to an aqueous composition for ophthalmological use or otolaryngological use (an aqueous ophthalmic composition or an aqueous otological composition).

BACKGROUND ART

Allergies are known to be developed by various causes such as pollen, dust, ticks, molds, pet hair, contact lenses, and cosmetics. An allergy developed by pollen, among others, is known as pollinosis. Pollinosis develops as a result of contact of mucous membrane or the like with pollen protein, which acts as an antigen, present in pollens. In recent years, the number of allergic sufferers is increasing, and therefore, development of a composition capable of preventing an allergy such as pollinosis, or otherwise capable of inhibiting exacerbation of pollinosis is desired. For example, Patent Literature 1 discloses a collyrium containing a carboxyvinyl polymer and monoterpene, whose amount used in contact with a washed site at one time is 500 µl or more.

CITATION LIST

Patent Literature

Patent Literature 1: Japanese Unexamined Patent Application Publication No. 2011-093889

SUMMARY OF INVENTION

Problems to be Solved by the Invention

The collyrium described in Patent Literature 1 is capable of removing foreign materials, such as pollen, dust, and cosmetics (e.g., mascara, eyeliner, eye shadow, lotion, milky lotion, and eye cream), attached to an eyeball (in particular, a cornea). Meanwhile, a method for removing pollen or the like more simply and more effectively is still desired.

An object of the present invention is to provide an aqueous composition for ophthalmological use or otolaryngological use having an excellent pollen removal effect.

Means for Solving the Problems

The inventors have found that an aqueous composition containing (A) a petrolatum and two or more (B) nonionic surfactants is capable of simply and effectively removing pollen attached to an ophthalmic or nasal mucosa.

Petrolatum is a kind of non-polar oil, and is a component that has long been generally used primarily as an ointment base. Also in the field of ophthalmology, petrolatum is generally used as an ophthalmic ointment base. However, no aqueous composition containing petrolatum has been known in the fields of ophthalmology and otolaryngology. A study conducted by the inventors has revealed a problem in that, for example, use of one surfactant as a solubilizing agent in preparing an aqueous composition containing petrolatum still results in separation or precipitation of an oil layer, and is thus incapable of allowing the petrolatum to dissolve to a sufficient degree. Meanwhile, the inventors have also found that an aqueous composition containing (A) a petrolatum and two or more (B) nonionic surfactants is capable of inhibiting separation and precipitation of an oil layer, and thus capable of significantly increasing the solubility of the petrolatum.

In addition, the inventors have also found that an aqueous composition containing (A) a petrolatum and two or more (B) nonionic surfactants is capable of reducing cell damage due to dry stress (dried damage) on mucous membrane cells of eyes, of nose, and the like.

The present invention was made based on the knowledge described above, and is directed to, for example, the aspects shown below.

[1] An aqueous composition for ophthalmological use or otolaryngological use, the aqueous composition containing: (A) a petrolatum; and two or more (B) nonionic surfactants.

[2] The aqueous composition according to [1], further containing: (C) a fat-soluble vitamin or vegetable oil.

[3] The aqueous composition according to [1] or [2], containing: (B-1) a nonionic surfactant having an HLB value of 10 or more; and (B-2) a nonionic surfactant having an HLB value of less than 10.

[4] The aqueous composition according to any one of [1] to [3], wherein (A) the petrolatum is white petrolatum.

[5] The aqueous composition according to any one of [2] to [4], wherein (C) the fat-soluble vitamin or vegetable oil is a vitamin E compound, a vitamin A compound, sesame oil, castor oil, olive oil, soybean oil, peanut oil, almond oil, wheat germ oil, camellia oil, corn oil, rape-seed oil, sunflower oil, cottonseed oil, or palm oil.

[6] The aqueous composition according to any one of [1] to [5], further containing: (D) a buffer.

[7] The aqueous composition according to any one of [1] to [6], wherein light transmittance at a wavelength of 660 nm is 60% or higher.

[8] The aqueous composition according to any one of [1] to [7], wherein a content of (A) the petrolatum relative to a total amount of the aqueous composition is in a range of from 0.0001 to 1% w/v.

[9] The aqueous composition according to any one of [1] to [8], for use in preventing, curing, ameliorating, or reducing an allergic symptom.

[10] An agent for preventing, curing, ameliorating, or reducing an allergic symptom, the agent containing: an aqueous composition for ophthalmological use or otolaryngological use, containing (A) a petrolatum and two or more (B) nonionic surfactants.

[11] Use of (A) a petrolatum and two or more (B) nonionic surfactants in preparing an aqueous composition for ophthalmological use or otolaryngological use for preventing, curing, ameliorating, or reducing an allergic symptom.

[12] A method for imparting an effect of preventing, curing, ameliorating, or reducing an allergic symptom to an aqueous composition for ophthalmological use or otolaryngological use, the method containing: preparing the aqueous composition for ophthalmological use or otolaryngological use, wherein the aqueous composition contains (A) a petrolatum and two or more (B) nonionic surfactants.

[13] A method for preparing an aqueous composition for ophthalmological use or otolaryngological use containing (A) a petrolatum that is solubilized and is not separative, the method containing: including (A) a petrolatum and two or more (B) nonionic surfactants in the aqueous composition.

[14] An agent for preventing, curing, ameliorating, or reducing a dry eye symptom, the agent containing: an aqueous composition for ophthalmological use containing (A) a petrolatum and two or more (B) nonionic surfactants.

[15] Use of (A) a petrolatum and two or more (B) nonionic surfactants in preparing an aqueous composition for ophthalmological use for use in preventing, curing, ameliorating, or reducing a dry eye symptom.

[16] A method for imparting an effect of preventing, curing, ameliorating, or reducing a dry eye symptom to an aqueous composition for ophthalmological use, the method containing: preparing the aqueous composition for ophthalmological use, wherein the aqueous composition contains (A) a petrolatum and two or more (B) nonionic surfactants.

[2-1] An aqueous composition for otolaryngological use, containing (A) a petrolatum and being contained in a container having a spray nozzle.

[2-2] The aqueous composition for otolaryngological use according to [2-1], further containing one or more (B) nonionic surfactants.

[2-3] The aqueous composition for otolaryngological use according to [2-1] or [2-2], wherein the aqueous composition for otolaryngological use is the aqueous composition according to any one of [1] to [9].

[2-4] The aqueous composition for otolaryngological use according to any one of [2-1] to [2-3], wherein the aqueous composition is a nasal drop or a nasal wash.

[2-5] An agent for relieving or reducing irritation upon application, wherein the agent includes the aqueous composition for otolaryngological use according to any one of [2-1] to [2-4].

[2-6] Use of (A) a petrolatum in preparing an aqueous composition for otolaryngological use, contained in a container having a spray nozzle, and for use in relieving or reducing irritation upon application.

[2-7] The use according to [2-6], wherein the aqueous composition for otolaryngological use is the aqueous composition for otolaryngological use according to any one of [2-1] to [2-4].

[2-8] A method for imparting an effect of relieving or reducing irritation upon application to an aqueous composition for otolaryngological use, the method including preparing the aqueous composition for otolaryngological use according to any one of [2-1] to [2-4].

The present invention can also be viewed as the methods described below.

[3-1] A method for preventing, curing, ameliorating, or reducing an allergic symptom, the method including douching an ophthalmic or nasal mucosa with an aqueous composition containing (A) a petrolatum and two or more (B) nonionic surfactants.

[3-2] A method for reducing dried damage of an ophthalmic mucosa cell, the method including allowing, to contact with the ophthalmic mucosa, an aqueous composition containing (A) a petrolatum and two or more (B) nonionic surfactants.

[3-3] A method for preventing, curing, ameliorating, or reducing a dry eye symptom, the method including allowing, to contact with an ophthalmic mucosa, an aqueous composition containing (A) a petrolatum and two or more (B) nonionic surfactants.

[3-4] A method for relieving or reducing irritation when an aqueous composition is applied to a nasal cavity mucosa or to an ear, the method including using (A) a petrolatum in the aqueous composition.

[3-5] The method according to [3-4] further including storing the aqueous composition in a container having a spray nozzle.

Effects of the Invention

According to the present invention, an allergenic substance, such as pollen, attached to a topical mucous membrane of an eye surface (e.g., a cornea), the nasal cavity, or the like can be simply and effectively removed. Thus, allergic symptoms, including pollinosis, due to an allergenic substance on a topical mucous membrane of eye, nose, or the like can be effectively prevented, cured, ameliorated, or reduced.

According to the present invention, despite containing petrolatum, an aqueous composition for ophthalmological or otolaryngological use can be provided in which oil layer separation or precipitation is inhibited, and thus the solubility of the petrolatum is significantly increased.

According to the present invention, cell damage due to dry stress in cells of ophthalmic and nasal mucosae, including corneal cells and the like, can be reduced or prevented. Therefore, freeing of an allergenic substance, such as histamine, caused by irritation, dry eye (dry condition of the eyes), and cell damage due to dry air-related symptoms can be inhibited, thereby allowing failures such as exacerbation of allergic symptoms to be reduced. Thus, an aqueous composition for ophthalmological or otolaryngological use that is comfortably administered and especially effective against dry eye and allergies can be provided.

According to the present invention, inclusion of petrolatum in an aqueous composition for otolaryngological use contained in a container having a spray nozzle can provide an aqueous composition for otolaryngological use that causes reduced irritation upon application and is comfortably administered.

EMBODIMENTS FOR CARRYING OUT THE INVENTION

Figure 1:
FIG. 1 is a set of photographs that show appearances of an aqueous composition of Reference Example 1 (left), and of an aqueous composition of Reference Example 2 (right), in Reference Test Example 1.
Figure 1:

Embodiments for carrying out the present invention will be described below in detail. It is to be understood, however, that the present invention is not limited to the embodiments presented below.

As used herein, the unit "%" of content denotes "% w/v," and is equivalent to "g/100 ml."

As used herein, an acronym "POE" means polyoxyethylene unless otherwise indicated.

As used herein, an acronym "POP" means polyoxypropylene unless otherwise indicated.

As used herein, a composition for ophthalmological use includes one applied to ophthalmic mucosae, and a composition for otolaryngological use includes one applied to at least one of nasal cavity mucosae and ears unless otherwise indicated. A composition for otolaryngological use is preferably one applied to nasal cavity mucosae.

[1. Aqueous Composition for Ophthalmological or Otolaryngological Use]

An aqueous composition for ophthalmological or otolaryngological use according to this embodiment contains (A) a petrolatum (hereinafter also referred to simply as "component (A)"), and two or more (B) nonionic surfactants (hereinafter also referred to simply as "components (B)").

Component (A)

As used herein, the term "petrolatum" is intended to include yellow petrolatum, obtained by purification of a mixture of hydrocarbons obtained from petroleum, and white petrolatum, obtained by decolorization and further purification.

A commercially available petrolatum may be used as the petrolatum without limitation. Specific examples of the petrolatum include, for example, Perfecta, Protopet Alba, Protopet White 15, White Fonoline, Protopet White 2L, Protopet White 3C, Yellow Fonoline, Protopet Yellow 1E, Protopet Yellow 2A, Protopet Super White (these are produced by Witco Corporation), Penreco Ultima, Penreco Super, Penreco Snow, Penreco Regent, Penreco Lily, Penreco Cream, Penreco Royal, Penreco Blond, Penreco Amber, Penreco 4650, Penreco Snow V, Ointment Base No. 4, No. 6, No. 8 (these are produced by Penreco), Perlatum 330, Perlatum 310/410, Perlatum 320/420, Perlatum 321, Perlatum 325/425, Perlatum 325/415 (these are produced by IGI), Snowwhite brand line of products such as Snowwhite Spetial and Snowwhite A4, Microwax MA, Sonnecone CM, Sonnecone DM, White Fonoline H, White Protopet 1 SH (these are produced by Sonnebom), white petrolatum adapted to Japanese Pharmacopoeia standard (those produced by Maruishi Pharmaceutical Co., Ltd., NIKKO Pharmaceutical Co., Ltd., etc.), yellow petrolatum adapted to Japanese Pharmacopoeia standard (those produced by Maruishi Pharmaceutical Co., Ltd., NIKKO Pharmaceutical Co., Ltd., etc.), Crolatum V (produced by Croda Japan KK), Sunwhite P-1, Sunwhite P-150, Sunwhite P-200, Sunwhite S-200 (these are produced by Nikko Rica Corporation), Nomcort W (produced by The Nisshin OilliO Group, Ltd.), and Propeto (produced by Maruishi Pharmaceutical Co., Ltd.). Further purified products thereof may also be used. These petrolatums may be used alone or in combination of any two or more thereof.

Among others, in view of higher achievement of the pollen removal effect, oil layer separation/precipitation inhibition effect, dry air-related cell damage reduction/prevention effect, and irritation reduction effect upon application of nasal drop, of the present invention, white petrolatum adapted to Japanese Pharmacopoeia standard, 16th revision, is preferred.

The content of the component (A) in the aqueous composition for ophthalmological or otolaryngological use according to this embodiment is not particularly limited, and is determined as appropriate depending on factors such as the application and the form of preparation of the aqueous composition for ophthalmological or otolaryngological use. Among others, in view of higher achievement of the pollen removal effect, oil layer separation/precipitation inhibition effect, dry air-related cell damage reduction/prevention effect, and irritation reduction effect upon application of nasal drop, of the present invention, the lower limit of the content of the component (A) is selected such that, for example, the total content of the component (A) relative to the total amount of the aqueous composition for ophthalmological or otolaryngological use may be 0.00001% w/v or more, and is preferably 0.0001% w/v or more, more preferably 0.0005% w/v or more, further preferably 0.001% w/v or more, and particularly preferably 0.005% w/v or more. The upper limit of the content of the component (A) is not particularly limited, but, for example, the total content of the component (A) relative to the total amount of the aqueous composition for ophthalmological or otolaryngological use may be 10% w/v or less, and is preferably 5% w/v or less, more preferably 1% w/v or less, further preferably 0.1% w/v or less, still more preferably 0.05% w/v or less, and particularly preferably 0.02% w/v or less. Any suitable combination of these upper and lower limits may be used.

In view of higher achievement of the pollen removal effect, oil layer separation/precipitation inhibition effect, dry air-related cell damage reduction/prevention effect, and irritation reduction effect upon application of nasal drop, of the present invention, the specific range of the content of the component (A) is selected such that, for example, the total content of the component (A) relative to the total amount of the aqueous composition for ophthalmological or otolaryngological use may be from 0.00001 to 10% w/v, and is preferably from 0.0001 to 1% w/v, more preferably from 0.0005 to 1% w/v, and further preferably from 0.001 to 0.1% w/v.

Component (B)

The nonionic surfactants are not particularly limited as long as they are medically, pharmaceutically (pharmacologically), or physiologically acceptable. Examples of the nonionic surfactant specifically include, for example, POE sorbitan fatty acid esters, such as POE (20) sorbitan monolaurate (polysorbate 20), POE (20) sorbitan monooleate (polysorbate 80), POE sorbitan monostearate (polysorbate 60), and POE sorbitan tristearate (polysorbate 65); POE hydrogenated castor oils, such as POE hydrogenated castor oil 5, POE hydrogenated castor oil 10, POE hydrogenated castor oil 20, POE hydrogenated castor oil 40, POE hydrogenated castor oil 50, POE hydrogenated castor oil 60, and POE hydrogenated castor oil 100; POE castor oils, such as POE castor oil 3, POE castor oil 4, POE castor oil 6, POE castor oil 7, POE castor oil 10, POE castor oil 13.5, POE castor oil 17, POE castor oil 20, POE castor oil 25, POE castor oil 30, POE castor oil 35, and POE castor oil 50; polyethylene glycol monostearates, such as polyethylene glycol monostearate (2 EO), polyethylene glycol monostearate (4 EO), polyethylene glycol monostearate (9 EO), polyethylene glycol monostearate (10 EO), polyethylene glycol monostearate (23 EO), polyethylene glycol monostearate (25 EO), polyethylene glycol monostearate (32 EO), polyethylene glycol monostearate (40 EO, polyoxyl 40 stearate), polyethylene glycol monostearate (45 EO), polyethylene glycol monostearate (55 EO), polyethylene glycol monostearate (75 EO), and polyethylene glycol monostearate (140 EO, polyoxyl 140 stearate); polyoxyethylene-polyoxypropylene block copolymers, such as POE (196)-POP (67) glycol (poloxamer 407, Pluronic F127), and POE (200)-POP (70) glycol; adducts of ethylenediamine and POE-POP block copolymers, such as poloxamine; POE alkyl ethers, such as POE (9) lauryl ether; POE-POP alkyl ethers, such as POE (20)-POP (4) cetyl ether; and POE alkyl phenyl ethers, such as POE (10) nonyl phenyl ether; and the like. The numbers in parentheses are the numbers of moles added.

The aqueous composition for ophthalmological or otolaryngological use according to this embodiment contains two or more (B) nonionic surfactants. The combination of (B) the nonionic surfactants is not particularly limited, but, in view of higher achievement of the effects of the present invention, this combination preferably includes one or more (B-1) nonionic surfactants each having an HLB value of 10 or more, and one or more (B-2) nonionic surfactants each having an HLB value of less than 10. In such case, the one or more (B-1) nonionic surfactants (hereinafter collectively or singly referred to as "(B-1) nonionic surfactant") each preferably have an HLB value of 11 or more, and more preferably an HLB value of 13 or more; and the one or more (B-2) nonionic surfactants (hereinafter collectively or singly referred to as "(B-2) nonionic surfactant") each preferably have an HLB value of 8 or less, and more preferably an HLB value of 6 or less.

Examples of (B-1) the nonionic surfactant having an HLB value of 10 or more (hereinafter also referred to simply as "component (B-1)") include, for example, POE sorbitan fatty acid esters, such as POE (20) sorbitan monolaurate (polysorbate 20), POE (20) sorbitan monooleate (polysorbate 80), POE sorbitan monostearate (polysorbate 60), and POE sorbitan tristearate (polysorbate 65); POE hydrogenated castor oils having 20 moles or more of ethylene oxide added on average, such as POE hydrogenated castor oil 20, POE hydrogenated castor oil 40, POE hydrogenated castor oil 50, POE hydrogenated castor oil 60, and POE hydrogenated castor oil 100; POE castor oils having 23 moles or more of ethylene oxide added on average, such as POE castor oil 25, POE castor oil 30, POE castor oil 35, and POE castor oil 50; polyethylene glycol monostearates having 7 moles or more of ethylene oxide added on average, such as polyethylene glycol monostearate (9 EO), polyethylene glycol monostearate (10 EO), polyethylene glycol monostearate (23 EO), polyethylene glycol monostearate (25 EO), polyethylene glycol monostearate (32 EO, polyethylene glycol monostearate (40 EO, polyoxyl 40 stearate), polyethylene glycol monostearate (45 EO), polyethylene glycol monostearate (55 EO), polyethylene glycol monostearate (75 EO), and polyethylene glycol monostearate (140 EO); and POE (196)-POP (67) glycol (poloxamer 407, Pluronic F127), POE (200)-POP (70) glycol, poloxamine, POE (20)-POP (4) cetyl ether, and POE (10) nonyl phenyl ether. Among these, in view of higher achievement of the pollen removal effect, oil layer separation/precipitation inhibition effect, dry air-related cell damage reduction/prevention effect, and irritation reduction effect upon application of nasal drop, of the present invention, preference is given to POE (20) sorbitan monooleate (polysorbate 80), POE hydrogenated castor oil 40, POE hydrogenated castor oil 60, POE castor oil 35, polyoxyl 40 stearate, polyoxyl 140 stearate, POE (196)-POP (67) glycol (poloxamer 407, Pluronic F127), and POE (200)-POP (70) glycol; and POE (20) sorbitan monooleate (polysorbate 80) and POE hydrogenated castor oil 60 are more preferred.

Examples of (B-2) the nonionic surfactant having an HLB value of less than 10 (hereinafter also referred to simply as "component (B-2)") include, for example, POE hydrogenated castor oils having less than 20 moles of ethylene oxide added on average, such as POE hydrogenated castor oil 5 and POE hydrogenated castor oil 10; POE castor oils having less than 23 moles of ethylene oxide added on average, such as POE castor oil 3, POE castor oil 4, POE castor oil 6, POE castor oil 7, POE castor oil 10, POE castor oil 13.5, POE castor oil 17, and POE castor oil 20; and polyethylene glycol monostearates having less than 7 moles of ethylene oxide added on average, such as polyethylene glycol monostearate (2 EO) and polyethylene glycol monostearate (4 EO). Among these, in view of higher achievement of the pollen removal effect, oil layer separation/precipitation inhibition effect, dry air-related cell damage reduction/prevention effect, and irritation reduction effect upon application of nasal drop, of the present invention, POE hydrogenated castor oils having less than 20 moles of ethylene oxide added on average, and POE castor oils having less than 23 moles of ethylene oxide added on average are preferred; POE castor oils having less than 23 moles of ethylene oxide added on average are more preferred; POE castor oil 3 and POE castor oil 10 are further preferred; and POE castor oil 3 is particularly preferred.

The content of the components (B) in the aqueous composition for ophthalmological or otolaryngological use according to this embodiment is not particularly limited, and is determined as appropriate depending on factors such as the application and the form of preparation of the aqueous composition for ophthalmological or otolaryngological use. In view of higher achievement of the pollen removal effect, oil layer separation/precipitation inhibition effect, dry air-related cell damage reduction/prevention effect, and irritation reduction effect upon application of nasal drop, of the present invention, the lower limit of the content of the components (B) is selected such that, for example, the total content of the components (B) relative to the total amount of the aqueous composition for ophthalmological or otolaryngological use may be 0.0001% w/v or more, and is preferably 0.001% w/v or more, more preferably 0.01% w/v or more, and further preferably 0.1% w/v or more. The upper limit of the content of the components (B) is not particularly limited, but, for example, the total content of the components (B) relative to the total amount of the aqueous composition for ophthalmological or otolaryngological use may be 20% w/v or less, and is preferably 10% w/v or less, more preferably 5% w/v or less, and further preferably 1% w/v or less.

In view of higher achievement of the pollen removal effect, oil layer separation/precipitation inhibition effect, dry air-related cell damage reduction/prevention effect, and irritation reduction effect upon application of nasal drop, of the present invention, the specific range of the content of the components (B) is selected such that, for example, the total content of the components (B) relative to the total amount of the aqueous composition for ophthalmological or otolaryngological use may be from 0.0001 to 20% w/v, and is preferably from 0.001 to 10% w/v, more preferably from 0.01 to 5% w/v, and further preferably from 0.1 to 1% w/v.

When (B-1) a nonionic surfactant having an HLB value of 10 or more, and (B-2) a surfactant having an HLB value of less than 10 are used in combination, in view of higher achievement of the pollen removal effect, oil layer separation/precipitation inhibition effect, dry air-related cell damage reduction/prevention effect, and irritation reduction effect upon application of nasal drop, of the present invention, the contents of the component (B-1) and of the component (B-2) are given as follows by way of example.

(B-1) Nonionic surfactant having an HLB value of 10 or more: the total content of the component (B-1) relative to the total amount of the aqueous composition for ophthalmological or otolaryngological use may be in a range of from 0.0001 to 10% w/v, and is preferably in a range of from 0.001 to 7% w/v, more preferably from 0.01 to 4% w/v, and further preferably from 0.1 to 1% w/v.

(B-2) Nonionic surfactant having an HLB value of less than 10: the total content of the component (B-2) relative to the total amount of the aqueous composition for ophthalmological or otolaryngological use may be in a range of from 0.0001 to 10% w/v, and is preferably in a range of from 0.001 to 5% w/v, more preferably from 0.005 to 1% w/v, and further preferably from 0.01 to 0.5% w/v.

In view of higher achievement of the pollen removal effect, oil layer separation/precipitation inhibition effect, dry air-related cell damage reduction/prevention effect, and irritation reduction effect upon application of nasal drop, of the present invention, the ratio between the amounts of the component (A) and of the components (B) in the aqueous composition for ophthalmological or otolaryngological use according to this embodiment is selected such that, for example, the total amount of the components (B) may be in a range of from 1 to 1000000 parts by mass, and is preferably in a range of from 10 to 100000 parts by mass, and more preferably from 100 to 10000 parts by mass, each per 100 parts by mass of the total amount of the component (A).

When (B-1) the nonionic surfactant having an HLB value of 10 or more and (B-2) the surfactant having an HLB value of less than 10 are used in combination, in view of higher achievement of the pollen removal effect, oil layer separation/precipitation inhibition effect, dry air-related cell damage reduction/prevention effect, and irritation reduction effect upon application of nasal drop, of the present invention, the ratio between the amounts of the component (A) and of the components (B) is given as follows by way of example.

The ratio between the amounts of the component (B-1) and of the component (B-2) in the aqueous composition for ophthalmological or otolaryngological use according to this embodiment is selected such that, for example, the total amount of the component (B-2) may be in a range of from 0.1 to 100000 parts by mass, and is preferably from 1 to 10000 parts by mass, and more preferably from 10 to 1000 parts by mass, each per 100 parts by mass of the total amount of the component (B-1).

In view of higher achievement of the pollen removal effect, oil layer separation/precipitation inhibition effect, dry air-related cell damage reduction/prevention effect, and irritation reduction effect upon application of nasal drop, of the present invention, the ratio between the amounts of the component (A) and of the component (B-1) in the aqueous composition for ophthalmological or otolaryngological use according to this embodiment is selected such that, for example, the total amount of the component (B-1) may be in a range of from 1 to 1000000 parts by mass, and is preferably from 10 to 100000 parts by mass, and more preferably from 100 to 10000 parts by mass, each per 100 parts by mass of the total amount of the component (A).

In view of higher achievement of the pollen removal effect, oil layer separation/precipitation inhibition effect, dry air-related cell damage reduction/prevention effect, and irritation reduction effect upon application of nasal drop, of the present invention, the ratio between the amounts of the component (A) and of the component (B-2) in the aqueous composition for ophthalmological or otolaryngological use according to this embodiment is selected such that, for example, the total amount of the component (B-2) may be in a range of from 1 to 1000000 parts by mass, and is preferably from 10 to 100000 parts by mass, and more preferably from 100 to 10000 parts by mass, each per 100 parts by mass of the total amount of the component (A).

Component (C)

The aqueous composition for ophthalmological or otolaryngological use according to this embodiment preferably further contains (C) at least one (hereinafter also referred to simply as "component (C)") selected from the group consisting of fat-soluble vitamins and vegetable oils. Further containing the component (C) permits higher achievement of the pollen removal effect, oil layer separation/precipitation inhibition effect, dry air-related cell damage reduction/prevention effect, and irritation reduction effect upon application of nasal drop, of the present invention, according to the present invention.

Examples of the fat-soluble vitamins specifically include, for example, vitamin E compounds, vitamin A compounds, derivatives thereof, and salts thereof.

Vitamin E compounds are not particularly limited as long as they are medically, pharmaceutically (pharmacologically), or physiologically acceptable. Examples of vitamin E compounds specifically include, for example, tocopherols, tocotrienols, derivatives thereof, and salts thereof. Tocopherols and tocotrienols may each be any of α-, β-, γ-, and δ-isomers, and be either the d- or dl-isomer. Examples of the salts thereof include, for example, salts of organic acids (lactates, acetates, butyrates, trifluoroacetates, fumarates, maleates, tartrates, citrates, succinates, malonates, methansulfonates, toluenesulfonates, tosilates, palmitates, stearates, etc.); inorganic salts (e.g., hydrochlorides, sulfates, nitrates, hydrobromides, phosphates, etc.); salts with organic bases (e.g., salts with organic amines such as methylamine, triethylamine, triethanolamine, morpholine, piperazine, pyrrolidine, amino acids, tripyridine, picoline, etc.); and salts with inorganic bases (e.g., ammonium salts; salts with alkali metals such as sodium and potassium, with alkaline-earth metals such as calcium and magnesium, and with metals such as aluminum; etc.). Examples of the derivatives thereof include, for example, esters such as acetic esters, nicotinic esters, succinic esters, and linolenic esters. The vitamin E compounds may be either natural or synthetic.

Examples of the vitamin E compounds more specifically include, for example, α-tocopherol such as d-α-tocopherol and dl-α-tocopherol, β-tocopherol, γ-tocopherol, δ-tocopherol, vitamin E acetate esters (e.g., tocopherol acetates), vitamin E nicotinate esters, vitamin E succinate esters, vitamin E linoleate esters, and the like. Among these, tocopherol acetates (e.g., d-α-tocopherol acetate, dl-α-tocopherol acetate, etc.) are preferred.

These vitamin E compounds may be used alone or in combination of any two or more thereof.

Vitamin A compounds are not particularly limited as long as they are medically, pharmaceutically (pharmacologically), or physiologically acceptable. Examples of vitamin A compounds include, for example, vitamin A, mixtures containing vitamin A (e.g., vitamin A oils), and vitamin A-active derivatives thereof. Note that a vitamin A oil is a fatty oil obtained from aquatic animal tissues or the like, containing retinol; a condensate thereof; or one to which vegetable oil has been added as appropriate. Examples of vitamin A compounds specifically include, for example, retinal, retinol, retinoic acid, carotin, dehydroretinal, lycopene, derivatives thereof, and salts thereof (e.g., retinol acetate, retinol palmitate, etc.). Among these, retinol acetate and retinol palmitate are preferred. The vitamin A compounds may be either natural or synthetic.

Examples of the vitamin A compounds include, for example, a retinol palmitate ester produced by DSM, 0.550 μg of which corresponds to 1 IU of vitamin A. IU is an International Unit; a value expressed in IU is obtained by a procedure described in, for example, Vitamin A Assay in Japanese Pharmacopoeia, 16th revision.

These vitamin A compounds may be used alone or in combination of any two or more thereof.

Examples of the vegetable oils include, for example, sesame oil, castor oil, olive oil, soybean oil, peanut oil, almond oil, wheat germ oil, *camellia* oil, corn oil, rape-seed oil, sunflower oil, cottonseed oil, and palm oil. The vegetable oils may be commercially available products. These vegetable oils may be used alone or in combination of any two or more thereof.

The term "sesame oil" collectively refers to vegetable oils obtained from seeds of plants classified in the genus *Sesamum* of the family Pedaliaceae (e.g., *Sesamum indicum* Linne (Pedaliaceae)). Sesame oil is obtainable from such seed by using a known pressing method and a known refinement method. For example, the sesame oil listed in Japanese Pharmacopoeia (see Commentary on Japanese Pharmacopoeia, 16th revision, C-1660 to 1662) is obtainable by refining oil that is collected using a cold-pressed method.

The term "castor oil" collectively refers to vegetable oils obtained from seeds of plants classified in the genus *Ricinus* of the family Euphorbiaceae (e.g., *Ricinus communis* Linne (Euphorbiaceae)). Castor oil is obtainable from such seed by using a known pressing method and a known refinement method. For example, the castor oil listed in Japanese Pharmacopoeia (see Commentary on Japanese Pharmacopoeia, 16th revision, C-3748 to 3751) is obtainable by collecting oil using a commonly used compression process, removing oil residue by centrifugation, decolorizing the resultant oil with activated earth, performing steam distillation at a high temperature (200 to 220° C.) under high vacuum, and then performing deacidification and deodorization for refinement.

The term "olive oil" collectively refers to vegetable oils obtained from fruit of plants classified in the genus *Olea* of the family Oleaceae (e.g., *Olea europaea* Linne (Oleaceae)). Olive oil is obtainable from fruit by using a known pressing method and a known refinement method. For example, the olive oil listed in Japanese Pharmacopoeia (see Commentary on Japanese Pharmacopoeia, 16th revision, C-1036 to 1039) is obtainable by collecting oil with a cold-pressed method (oil collection without heating) performed immediately on mature fruits, performing mechanical filtering or centrifugation, and then performing a normal refinement process.

The term "soybean oil" collectively refers to vegetable oils obtained from seeds of plants classified in the genus Glycine of the family Leguminosae (e.g., *Glycine max* Merrill (Leguminosae)). Soybean oil is obtainable from such seed by using a known pressing method and a known refinement method. For example, the soybean oil listed in Japanese Pharmacopoeia (see Commentary on Japanese Pharmacopoeia, 16th revision, C-2617 to 2618) is obtainable by crushing and flat-pressing soybeans (cold pressing or warm pressing is also usable for oil production), and performing an extraction method using a solvent (hexane).

The term "peanut oil" collectively refers to vegetable oils obtained from seeds of plants classified in the genus *Arachis* of the family Leguminosae (e.g., *Arachis hypogaea* Linne (Leguminosae)). Peanut oil is obtainable from such seed by using a known pressing method and a known refinement method. For example, the peanut oil listed in Japanese Pharmacopoeia (see Commentary on Japanese Pharmacopoeia, 16th revision, C-5093 to 5095) is obtainable by grinding seeds with a roller, followed by heating and compressing, and then filtering the obtained oil for refinement.

The term "almond oil" collectively refers to vegetable oils obtained from kernels of plants classified in the genus *Prunus* of the family Rosaceae (e.g., a variety of *Prunus amygdalus* Batsch (Rosaceae), sweet almond). Almond oil is obtainable from such kernels by using a known pressing method and a known refinement method (see, e.g., Japanese Pharmaceutical Excipients 2003, p. 93).

The term "wheat germ oil" collectively refers to vegetable oils obtainable from germ of plants classified in the genus *Triticum* of the family Gramdneae (e.g., *Triticum aestivum* Linne (Gramdneae)). Wheat germ oil is obtainable from such germ by using a known pressing method and a known refinement method (see, e.g., Japanese Pharmaceutical Excipients 2003, p. 306).

The term "*camellia* oil" collectively refers to vegetable oils obtained from seeds of plants classified in the genus *Camellia* of the family Theaceae (e.g., *Camellia japonica* Linne (Theaceae)). *Camellia* oil is obtainable from such seed by using a known pressing method and a known refinement method. For example, the *camellia* oil listed in Japanese Pharmacopoeia (see Commentary on Japanese Pharmacopoeia, 16th revision, C-2819 to 2820) is obtainable by grinding seeds dried in the sun or artificially, followed by steaming, compressing, and filtering the resultant for refinement.

The term "corn oil" collectively refers to vegetable oils obtainable from germ of plants classified in the genus *Zea* of the family Gramineae (e.g., *Zea mays* Linne (Gramineae)). Corn oil is obtainable from such germ by using a known pressing method and a known refinement method. For example, the corn oil listed in Japanese Pharmacopoeia (see Commentary on Japanese Pharmacopoeia, 16th revision, C-2986 to 2988) is obtainable by selecting germs from grains, washing the germs with water followed by rapid heating and drying, compressing the resultant germs, and then extracting oil from the pomace with hexane.

The term "rape-seed oil" collectively refers to vegetable oils obtained from seeds of plants classified in the genus *Brassica* of the family Cruciferae (e.g., *Brassica campestris* Linne subsp. *napus* Hooker filiuset Anderson var. nippo-oleifera Makino (Cruciferae)). Rape-seed oil is obtainable from such seed by using a known pressing method and a known refinement method. For example, the rape-seed oil listed in Japanese Pharmacopoeia (see Commentary on Japanese Pharmacopoeia, 16th revision, C-3239 to 3240) is typically produced by heating and compressing seeds, performing solvent extraction on the pomace, mixing the extracted oil with the compressed oil to produce raw oil, and refining the raw oil obtained.

The term "sunflower oil" collectively refers to vegetable oils obtained from seeds of plants classified in the genus *Helianthus* of the family Compositae (e.g., *Helianthus annuus* Linne (Compositae)). Sunflower oil is obtainable from such seed by using a known pressing method and a known refinement method (see, e.g., Japanese Pharmaceutical Excipients 2003, p. 523).

The term "cottonseed oil" collectively refers to vegetable oils obtained from seeds of plants classified in the genus *Gossypium* of the family Malvaceae (e.g., *Gossypium hirsutum* Linne (*Gossypium*), or a plant classified in the same genus (Malvaceae)). Cottonseed oil is obtainable from such seed by using a known pressing method and a known refinement method. For example, cottonseed oil is obtainable by refining nonvolatile fatty oil obtained by performing a compression or extraction process on seeds (see, e.g., Japanese Pharmaceutical Excipients 2003, p. 710).

The term "palm oil" collectively refers to vegetable oils obtained from seeds of plants classified in the genus *Cocos* of the family Palmae (e.g., *Cocos nucifera* Linne (Palmae)). Palm oil is obtainable from such seed by using a known pressing method and a known refinement method. For example, the palm oil listed in Japanese Pharmacopoeia (see Commentary on Japanese Pharmacopoeia, 16th revision, C-5017 to 5019) is obtained by grinding copura, further grinding the ground copra, steaming, compressing, and then removing suspended matter for refinement.

The component (C) may be used alone or in combination of any two or more thereof. The component (C) is preferably a vitamin E compound, a vitamin A compound, sesame oil, or castor oil, more preferably a vitamin E compound, sesame oil, or castor oil, and further preferably tocopherol acetate or sesame oil.

When the component (C) is used, the lower limit of the content of the component (C) in the aqueous composition for ophthalmological or otolaryngological use according to this embodiment is not particularly limited. However, in view of higher achievement of the pollen removal effect, oil layer separation/precipitation inhibition effect, dry air-related cell damage reduction/prevention effect, and irritation reduction effect upon application of nasal drop, of the present invention, the total content of the component (C) relative to the total amount of the aqueous composition for ophthalmological or otolaryngological use may be, for example, 0.00001% w/v or more, and is preferably 0.0001% w/v or more, more preferably 0.0005% w/v or more, and further preferably 0.005% w/v or more. The upper limit of the content of the component (C) is not particularly limited, but in view of higher achievement of the pollen removal effect, oil layer separation/precipitation inhibition effect, dry air-related cell damage reduction/prevention effect, and irritation reduction effect upon application of nasal drop, of the present invention, the total content of the component (C) relative to the total amount of the aqueous composition for ophthalmological or otolaryngological use may be, for example, 10% w/v or less, and is preferably 5% w/v or less, more preferably 1% w/v or less, and further preferably 0.5% w/v or less.

In view of higher achievement of the pollen removal effect, oil layer separation/precipitation inhibition effect, dry air-related cell damage reduction/prevention effect, and irritation reduction effect upon application of nasal drop, of the present invention, the specific range of the content of the component (C) is selected such that, for example, the total content of the component (C) relative to the total amount of the aqueous composition for ophthalmological or otolaryngological use may be from 0.00001 to 10% w/v, and is preferably from 0.0001 to 1% w/v, more preferably form 0.0005 to 1% w/v, and further preferably from 0.001 to 0.1% w/v.

In view of higher achievement of the pollen removal effect, oil layer separation/precipitation inhibition effect, dry air-related cell damage reduction/prevention effect, and irritation reduction effect upon application of nasal drop, of the present invention, the ratio between the amounts of the component (A) and of the component (C) in the aqueous composition for ophthalmological or otolaryngological use according to this embodiment is selected such that, for example, the total amount of the component (C) may be in a range of from 1 to 1000000 parts by mass, and is preferably in a range of from 10 to 100000 parts by mass, and more preferably from 100 to 10000 parts by mass, each per 100 parts by mass of the total amount of the component (A).

Component (D)

The aqueous composition for ophthalmological or otolaryngological use according to this embodiment preferably further contains (D) a buffer (hereinafter also referred to simply as "component (D)"). Further containing the component (D) permits higher achievement of the effects according to the present invention.

(D) The buffer is not particularly limited as long as it is medically, pharmaceutically (pharmacologically), or physiologically acceptable. Examples of (D) the buffer specifically include, for example, boric acid buffers, phosphoric acid buffers, carbonic acid buffers, citric acid buffers, acetic acid buffers, epsilon-aminocaproic acid, aspartic acid, and aspartates. Among these, boric acid buffers, phosphoric acid buffers, carbonic acid buffers, and citric acid buffers are preferred.

Examples of the boric acid buffers include, for example, boric acid, and borates such as alkali metal borates and alkaline-earth metal borates. Examples of the phosphoric acid buffers include, for example, phosphoric acid, and phosphates such as alkali metal phosphates and alkaline-earth metal phosphates. Examples of the carbonic acid buffers include, for example, carbonic acid, and carbonates such as alkali metal carbonates and alkaline-earth metal carbonates. Examples of the citric acid buffers include, for example, citric acid, alkali metal citrates, alkaline-earth metal citrates, and the like. A borate or phosphate hydrate may be used as a boric acid buffer or a phosphoric acid buffer, respectively. More specific examples include boric acid buffers such as, for example, boric acid and salts thereof (e.g., sodium borate, potassium tetraborate, potassium metaborate, ammonium borate, and borax); phosphoric acid buffers such as, for example, phosphoric acid and salts thereof (e.g., disodium hydrogen phosphate, sodium dihydrogen phosphate, potassium dihydrogen phosphate, trisodium phosphate, dipotassium phosphate, calcium monohydrogen phosphate, and calcium dihydrogen phosphate); carbonic acid buffers such as, for example, carbonic acid and salts thereof (e.g., sodium acid carbonate, sodium carbonate, ammonium carbonate, potassium carbonate, calcium carbonate, potassium acid carbonate, and magnesium carbonate); citric acid buffers such as, for example, citric acid and salts thereof (e.g., sodium citrate, potassium citrate, calcium citrate, sodium dihydrogen citrate, and disodium citrate); acetic acid buffers such as, for example, acetic acid and salts thereof (e.g., ammonium acetate, potassium acetate, calcium acetate, and sodium acetate); and aspartic acid and salts thereof (e.g., sodium aspartate, magnesium aspartate, and potassium aspartate). These buffers may be used alone or in combination of any two or more thereof.

Among the aforementioned buffers, boric acid buffers and phosphoric acid buffers are particularly preferred. The boric acid buffer used is preferably a combination of boric acid and a salt thereof, more preferably a combination of boric acid and an alkali metal borate and/or alkaline-earth metal borate, further preferably a combination of boric acid and an alkali metal borate, and still more preferably a combination of boric acid and borax. The phosphoric acid buffer used is preferably a combination of a primary phosphate and a secondary phosphate, more preferably a combination of an alkali metal primary phosphate and an alkali metal secondary phosphate, and further preferably a combination of sodium dihydrogen phosphate and disodium hydrogen phosphate. In view of higher achievement of the effects according to the present invention, use of a boric acid buffer is particularly preferred.

When the component (D) is used, the content of the component (D) in the aqueous composition for ophthalmological or otolaryngological use according to this embodiment depends on factors such as the component (D) used, the other components and the amounts thereof, and the application and the form of preparation of the aqueous composition for ophthalmological or otolaryngological use, and thus cannot be defined as a constant value. However, for example, the total content of the component (D) relative to the total amount of the aqueous composition for ophthalmological or otolaryngological use may be in a range of from 0.01 to 10% w/v, and is preferably in a range of from 0.1 to 5% w/v, and more preferably from 0.2 to 2% w/v.

The aqueous composition for ophthalmological or otolaryngological use according to this embodiment preferably further contains a terpenoid compound. The terpenoid compound is not particularly limited as long as it is medically, pharmaceutically (pharmacologically), or physiologically acceptable. Examples of the terpenoid compound specifically include, for example, menthol, camphor, borneol, geraniol, cineol, citronellol, menthone, carvone, anethole, eugenol, limonene, linalool, linalyl acetate, and derivatives thereof. The terpenoid compounds may each be any of the d-, l-, and dl-isomers. An essential oil containing a terpenoid compound may be used as the terpenoid compound. Examples of such essential oils include, for example, *eucalyptus* oil, bergamot oil, peppermint oil, cool mint oil, spearmint oil, mentha oil, fennel oil, cinnamon oil, and rose oil. These terpenoid compounds may be used alone or in combination of any two or more thereof.

Among the terpenoid compounds, in view of higher achievement of the effects according to the present invention, preference is given to dl-menthol, 1-menthol, dl-camphor, d-camphor, d-borneol or geraniol. Examples of essential oils containing these terpenoid compounds include, for example, cool mint oil, peppermint oil, mentha oil, and camphor oil. The terpenoid compound used is more preferably dl-menthol, 1-menthol, dl-camphor, d-camphor, d-borneol geraniol, further preferably 1-menthol, d-camphor, or dl-camphor, and still more preferably 1-menthol.

When a terpenoid compound is used, the content of the terpenoid compound in the aqueous composition for ophthalmological or otolaryngological use according to this embodiment depends on factors such as the terpenoid compound used, the other components and the amounts thereof; and the application and the form of preparation of the aqueous composition for ophthalmological or otolaryngological use, and thus cannot be defined as a constant value. However, for example, the total content of the terpenoid compound relative to the total amount of the aqueous composition for ophthalmological or otolaryngological use may be in a range of from 0.0001 to 10% w/v, and is preferably in a range of from 0.0001 to 5% w/v, more preferably from 0.0005 to 5% w/v, further preferably from 0.001 to 3% w/v, still more preferably from 0.001 to 1% w/v, and particularly preferably from 0.001 to 0.1% w/v.

The aqueous composition for ophthalmological or otolaryngological use according to this embodiment preferably further contains a thickener. The thickener is not particularly limited as long as it is medically, pharmaceutically (pharmacologically), or physiologically acceptable. Examples of the thickener specifically include, for example, vinyl-based thickeners [e.g., (completely or partially saponified) polyvinyl alcohols, polyvinyl pyrrolidone (K25, K30, K90, etc.), and carboxyvinyl polymers], cellulose-based thickeners [e.g., methyl cellulose, ethyl cellulose, hydroxyethyl cellulose, hydroxypropyl cellulose, hydroxypropyl methyl cellulose (2208, 2906, 2910, etc.), carboxymethyl cellulose, carboxyethyl cellulose, nitrocellulose, and salts thereof], polyethylene glycol (macrogol 300, macrogol 400, macrogol 1500, macrogol 4000, etc.), and mucopolysaccharides [e.g., chondroitin sulfuric acid, alginic acid, hyaluronic acid, and salts thereof], and polysaccharides [e.g., guar gum, hydroxypropyl guar gum, gum arabic, karaya gum, xanthan gum, carrageenan, agar, alginic acid, α-cyclodextrin, dextrin, dextran, starch, chitin and derivatives thereof, and chitosan and derivatives thereof]. Examples of salts of the thickeners include, for example, salts with inorganic bases. The salt of the thickener is preferably an alkali metal salt or an alkaline-earth metal salt, more preferably a sodium salt, a potassium salt, a calcium salt, or a magnesium salt, and further preferably a sodium salt. These thickeners may be used alone or in combination of any two or more thereof.

Among these thickeners, in view of higher achievement of the effects according to the present invention, vinyl-based thickeners, cellulose-based thickeners, polyethylene glycol, and mucopolysaccharides are preferred. Examples of the vinyl-based thickeners include, for example, polyvinyl alcohols, polyvinyl pyrrolidone, and carboxyvinyl polymers. Examples of the cellulose-based thickeners include, for example, methyl cellulose, hydroxyethyl cellulose, hydroxypropyl cellulose, hydroxypropyl methyl cellulose, carboxymethyl cellulose, and salts thereof. Examples of polyethylene glycol include, for example, macrogol 300 and macrogol 400. Examples of the mucopolysaccharides include chondroitin sulfuric acid and salts thereof, alginic acid and salts thereof, and hyaluronic acid and salts thereof. The thickener used is more preferably a carboxyvinyl polymer, hydroxypropyl methyl cellulose, hydroxyethyl cellulose, polyvinyl pyrrolidone, polyvinyl alcohol, sodium alginate, or sodium hyaluronate; further preferably polyvinyl pyrrolidone (K25 and K90), a carboxyvinyl polymer, hydroxyethyl cellulose, hydroxypropyl methyl cellulose (2208, 2906, and 2910), sodium chondroitin sulfate, or sodium hyaluronate; and still more preferably hydroxypropyl methyl cellulose, sodium chondroitin sulfate, or sodium hyaluronate.

When a thickener is used, the content of the thickener in the aqueous composition for ophthalmological or otolaryngological use according to this embodiment depends on factors such as the thickener used, the other components and the amounts thereof, and the application and the form of preparation of the aqueous composition for ophthalmological or otolaryngological use, and thus cannot be defined as a constant value. However, for example, the total content of the thickener relative to the total amount of the aqueous composition for ophthalmological or otolaryngological use may be in a range of from 0.01 to 10% w/v, and is preferably in a range of from 0.01 to 5% w/v, more preferably from 0.05 to 3% w/v, and further preferably from 0.1 to 1% w/v.

The aqueous composition for ophthalmological or otolaryngological use according to this embodiment may further contain an isotonizing agent. The isotonizing agent is not particularly limited as long as it is medically, pharmaceutically (pharmacologically), or physiologically acceptable. Examples of the isotonizing agent specifically include, for example, disodium hydrogen phosphate, sodium dihydrogen phosphate, potassium dihydrogen phosphate, sodium hydrogen sulfite, sodium sulfite, potassium chloride, calcium chloride, sodium chloride, magnesium chloride, potassium acetate, sodium acetate, sodium acid carbonate, sodium carbonate, sodium thio sulfate, and magnesium sulfate. Among these isotonizing agents, preference is given to potassium chloride, calcium chloride, sodium chloride, and magnesium chloride. These isotonizing agents may be used alone or in combination of any two or more thereof.

When an isotonizing agent is used, the content of the isotonizing agent in the aqueous composition for ophthalmological or otolaryngological use according to this embodiment depends on factors such as the isotonizing agent used, the other components and the amounts thereof, and the application and the form of preparation of the aqueous composition for ophthalmological or otolaryngological use, and thus cannot be defined as a constant value. However, for example, the total content of the isotonizing agent relative to the total amount the aqueous composition for ophthalmological or otolaryngological use may be in a range of from 0.01 to 10% w/v, and is preferably in a range of from 0.05 to 5% w/v, and more preferably from 0.1 to 2% w/v.

The pH of the aqueous composition for ophthalmological or otolaryngological use according to this embodiment is not particularly limited as long as it is medically, pharmaceutically (pharmacologically), or physiologically acceptable. For example, the pH of the aqueous composition for ophthalmological or otolaryngological use according to this embodiment may be in a range of from 4.0 to 9.5, and is preferably in a range of from 4.5 to 8.5, more preferably from 5.0 to 8.5, and further preferably from 5.5 to 7.5.

The aqueous composition for ophthalmological or otolaryngological use according to this embodiment may be adjusted as necessary to have an osmotic pressure ratio within a range acceptable to living organisms. The suitable osmotic pressure ratio depends on the applied site, the dosage form, and/or the like, but, for example, may be in a range of from 0.7 to 5.0, and is preferably in a range of from 0.9 to 3.0, and more preferably from 1.0 to 2.0. The osmotic pressure can be adjusted using a method known in the technical field using inorganic salt, polyalcohol, or the like. As used herein, an osmotic pressure ratio refers to a ratio of the osmotic pressure to 286 mOsm (the osmotic pressure of 0.9% w/v aqueous sodium chloride solution) according to Japanese Pharmacopoeia, 16th revision. An osmotic pressure is measured using, as reference, the osmolarity determination (freezing-point depression method) described in Japanese Pharmacopoeia. The standard solution for measuring an osmotic pressure ratio (0.9% w/v aqueous sodium chloride solution) can be prepared by drying sodium chloride (standard reagent described in Japanese Pharmacopoeia) for 40 to 50 minutes at 500 to 650° C., leaving the resultant to cool in a desiccator (silica gel), accurately weighing out 0.900 g thereof, and dissolving it in purified water to prepare exactly 100 ml of the solution; or by using commercially available standard solution for measuring an osmotic pressure ratio (0.9% w/v aqueous sodium chloride solution).

In addition to the components described above, the aqueous composition for ophthalmological or otolaryngological use according to this embodiment may contain appropriate amounts of components, in combination, selected from various pharmacologically active substances and physiologically active substances in amounts that would not impair the effects of the present invention. Such components are not particularly limited, but examples thereof include, for example, active ingredients in ophthalmologic or otolaryngologic drugs listed in Standards for Marketing Approval of Non-prescription Drugs 2012 (supervising editor: Society for Regulatory Science of Medical Products, General Incorporated Association). Examples of components used in ophthalmologic or otolaryngologic drugs specifically include, for example, the component as shown below.

Antihistamine: e.g., iproheptine, diphenhydramine, chlorpheniramine maleate, ketotifen fumarate, olopatadine hydrochloride, and levocabastine hydrochloride.

Antiallergic agent: e.g., sodium cromoglicate, tranilast, and pemirolast potassium.

Steroidal drug: e.g., fluticasone propionate, fluticasone furoate, mometasone furoate, beclometasone dipropionate, and flunisolide.

Vasoconstrictor (decongestant): e.g., tetrahydrozoline, naphazoline, epinephrine, ephedrine, methylephedrine, and phenylephrine.

Sterilizing agent: e.g., acrinol, cetylpyridinium, benzalkonium, benzethonium, chlorhexidine, and polyhexamethylene biguanide.

Vitamin: e.g., flavin adenine dinucleotide sodium, cyanocobalamin, pyridoxine hydrochloride, panthenol, and calcium pantothenate.

Amino acid: e.g., potassium aspartate, magnesium aspartate, magnesium potassium aspartate, and aminoethyl sulfonic acid.

Antiphlogistic: e.g., glycyrrhetinic acid, glycyrrhizic acid, pranoprofen, methyl salicylate, glycol salicylate, allantoin, tranexamic acid, ε-aminocaproic acid, berberine, sodium azulene sulfonate lysozyme, and glycyrrhiza.

Astringent: e.g., hydrozincite, zinc lactate, and zinc sulfate.

Local anesthetic: e.g., lidocaine.

Miscellaneous: e.g., sulfamethoxazole, indometacin, ibuprofen, ibuprofen piconol, bufexamac, butyl flufenamate, bendazac, piroxicam, ketoprofen, felbinac, lithospermum root, horse chestnut, and salts thereof.

The aqueous composition for ophthalmological or otolaryngological use according to this embodiment may contain appropriate amounts of one or more of various additives, in combination, appropriately selected in the usual manner, in amounts that would not impair the effects of the present invention depending on the application and the form of preparation thereof. Examples of such additives include, for example, a variety of additives listed in Japanese Pharmaceutical Excipients Directory 2007 (edited by the International Pharmaceutical Excipients Council Japan). Examples of typical components include the additives as shown below.

Carrier: e.g., water, and aqueous solvents such as hydrous ethanol.

Sugar: e.g., glucose.

Sugar alcohol: e.g., xylitol, sorbitol, and mannitol. These substances may each be any of the d-, l-, and dl-isomers.

Antiseptic, sterilizing agent, or antimicrobial agents: e.g., alkyl diaminoethyl glycine hydrochloride, sodium benzonate, ethanol, benzalkonium chloride, benzethonium chloride, chlorhexidine gluconate, chlorobutanol, sorbic acid, potassium sorbate, sodium dehydroacetate, methyl para-hydroxybenzonate, ethyl para-hydroxybenzonate, propyl para-hydroxybenzonate, butyl para-hydroxybenzonate, oxyquinoline sulfate, phenethyl alcohol, benzyl alcohol, biguanide compounds (specifically, polyhexamethylene biguanide, etc.), and Glokill (trade name, product of Rodhia).

Chelating agent: e.g., ethylenediaminediacetatic acid (EDDA), ethylenediaminetriacetatic acid, ethylenediaminetetraacetatic acid (edetic acid, EDTA), N-(2-hydroxyethyl)ethylenediaminetriacetatic acid (HEDTA), and diethylenetriaminepentaacetatic acid (DTPA).

Stabilizing agent: e.g., dibutylhydroxytoluene, trometamol, sodium formaldehyde sulfoxylate (rongalite), tocopherol, sodium pyrosulfite, monoethanol amine, aluminum monostearate, and glycerin monostearate.

Base: e.g., octyl dodecanol, titanium oxide, potassium bromide, liquid paraffin, plastibase, lanolin, and propylene glycol.

In this embodiment, the term "aqueous composition" means a composition containing 50% w/v or more of water relative to the total amount of that aqueous composition. The content of water in an aqueous composition is preferably 80% w/v or more, more preferably 90% w/v or more, further preferably 95% w/v or more, and still more preferably 97% w/v or more, relative to the total amount of the aqueous composition. When the aqueous composition is a composition for otolaryngological use, the content of water relative to the total amount of the aqueous composition may be 60% w/v or more, or 70% w/v or more. The water for use in the aqueous composition is not particularly limited as long as it is medically, pharmaceutically (pharmacologically), or physiologically acceptable. Examples of such water include, for example, distilled water, water, purified water, sterile purified water, water for injection, and distilled water for injection. The definitions thereof conform to Japanese Pharmacopoeia, 16th revision.

In this embodiment, the aqueous composition is preferably an aqueous composition for ophthalmological or otolaryngological use, used in the field of ophthalmology or otolaryngology.

The aqueous composition for ophthalmological or otolaryngological use according to this embodiment can be prepared by adding and mixing desired amounts of the component (A) and the components (B), and other component(s) as need, to achieve desired concentrations; more specifically, for example, by dissolving or suspending these components in purified water, adjusting the pH and the osmotic pressure to predetermined values, and, as needed, sterilizing the resultant by filter sterilization or other method. The component (A) and other highly hydrophobic component(s) may be dissolved by preliminarily adding the components (B) or a component having a solubilizing effect, stirring the resultant mixture, and then adding purified water.

The aqueous composition for ophthalmological or otolaryngological use according to this embodiment may be in various forms of preparation depending on its intended use. Examples of the form of preparation include, for example, a liquid preparation and a semisolid preparation (ointment etc.). The aqueous composition for ophthalmological or otolaryngological use according to this embodiment is preferably in a liquid preparation.

The aqueous composition for ophthalmological or otolaryngological use according to this embodiment may be used as, for example, eye drop (also referred to as ophthalmic solution or ophthalmic drug; the term "eye drop" includes eye drops applicable during wear of contact lenses), artificial tears, eye wash (also referred to as collyria or eye lotion; the term "eye wash" includes eye wash applicable during wear of contact lenses), solution for wearing contact lenses, contact lens care products (including, e.g., disinfectant solution, storage solution, cleaning solution, and cleaning-storage solution for contact lenses), ophthalmic ointment, nasal drop, nasal wash (also referred to as nasal douching), ear drop, and the like. The term "contact lenses" includes hard and soft contact lenses (including both ionic and nonionic ones, and including both silicone hydrogel contact lenses and non-silicone hydrogel contact lenses).

Among these, the amount of eye drop used in each application is very low. Therefore, variation in the content of a component in the preparation used in one time due to separation or the like has a large effect, and thus stable maintenance of the blended components is highly demanded. Despite containing petrolatum, the aqueous composition for ophthalmological or otolaryngological use according to this embodiment permits oil layer separation or precipitation to be inhibited, and thus the solubility of the petrolatum to be significantly increased. In view of such effect, the aqueous composition for ophthalmological or otolaryngological use according to this embodiment can be suitably used as an eye drop.

The aqueous composition for ophthalmological or otolaryngological use according to this embodiment is provided as being contained in a container generally used in the pharmaceutical field. The container may be made of either glass or plastic. The container may be a transparent container that allows the inside of the container to be seen, or an opaque container that prevents the inside of the container from being easily seen. As used herein, the term "transparent container" includes both colorless and colored transparent containers. The component material of a plastic container is not particularly limited, but may be, for example, one of polyethylenenaphthalate, polyarylate, polyethyleneterephthalate, polypropylene, polyethylene, and polyimide, one of copolymers thereof, or a mixture of two or more substances including these materials. Examples of these copolymers include copolymers containing one of ethylene-2,6-naphthalate unit, arylate unit, ethyleneterephthalate unit, propylene unit, ethylene unit, and imide unit.

The aqueous composition for ophthalmological or otolaryngological use according to this embodiment has improved solubility of petrolatum, and thus exhibits high light transmittance. Therefore, in order to allow visual verification that the preparation has high light transmittance, a transparent container is suitably used as the container for containing the aqueous composition for ophthalmological or otolaryngological use according to this embodiment. Containing the preparation in a transparent container having high light transmittance permits a foreign matter inspection to be easily conducted visually. Thus, the aqueous composition of the present invention is preferably used as, among others, an eye drop or a collyrium, which requires a foreign matter inspection. For example, the light transmittance at a wavelength of 660 nm of the aqueous composition for ophthalmological or otolaryngological use according to this embodiment may be 20% or higher, and is preferably 30% or higher, more preferably 50% or higher, further preferably 60% or higher, still more preferably 70% or higher, still further preferably 75% or higher, particularly preferably 80% or higher, particularly more preferably 85% or higher, and particularly still more preferably 90% or higher.

[2. Prevention, Cure, Amelioration, or Reduction of Allergic Symptoms]

The aqueous composition for ophthalmological or otolaryngological use according to this embodiment has an effect of washing out allergen, such as pollen, attached to a surface of an ophthalmic or nasal mucosa. Thus, the aqueous composition for ophthalmological or otolaryngological use according to this embodiment is useful for preventing, curing, ameliorating, or reducing allergic symptoms.

Thus, one embodiment of the present invention provides an agent for preventing, curing, ameliorating, or reducing allergic symptoms including an aqueous composition for ophthalmological or otolaryngological use that contains (A) a petrolatum and two or more (B) nonionic surfactants. Another embodiment of the present invention provides use of (A) a petrolatum and two or more (B) nonionic surfactants in preparing an aqueous composition for ophthalmological or otolaryngological use for use in preventing, curing, ameliorating, or reducing allergic symptoms. Still another embodiment of the present invention provides a method for imparting an effect of preventing, curing, ameliorating, or reducing allergic symptoms to an aqueous composition for ophthalmological or otolaryngological use, including preparing an aqueous composition for ophthalmological or otolaryngological use containing (A) a petrolatum and two or more (B) nonionic surfactants. Further, still another embodiment of the present invention provides a method for preventing, curing, ameliorating, or reducing allergic symptoms, including a step of douching an ophthalmic or nasal mucosa to be douched using an aqueous composition for ophthalmological or otolaryngological use containing (A) a petrolatum and two or more (B) nonionic surfactants. The step of douching permits effective removal of allergenic substances (e.g., pollen, dust, ticks, molds, pet hair, contact lenses, and cosmetics) present in the ophthalmic or nasal mucosa to be douched.

The component (A) and components (B) and the contents etc. thereof, the other components and the contents etc. thereof, the form of preparation and the application of the aqueous composition, etc. in each of the embodiments described above are as described in the section [1. Aqueous composition for ophthalmological or otolaryngological use].

[3. Reduction in Dried Damage of Ophthalmic Mucosa Cells]

The aqueous composition for ophthalmological or otolaryngological use according to this embodiment has an effect of reducing/preventing cell damage due to dry stress (dried damage).

Thus, one embodiment of the present invention provides an agent for reducing dried damage of an ophthalmic mucosa cell, containing an aqueous composition for ophthalmological use that contains (A) a petrolatum and two or more (B) nonionic surfactants. Another embodiment of the present invention provides use of (A) a petrolatum and two or more (B) nonionic surfactants in preparing an aqueous composition for ophthalmological use for use in reducing dried damage of an ophthalmic mucosa cell. Still another embodiment of the present invention provides a method for imparting an effect of reducing dried damage of an ophthalmic mucosa cell to an aqueous composition for ophthalmological use, including preparing an aqueous composition for ophthalmological use containing (A) a petrolatum and two or more (B) nonionic surfactants. Further, still another embodiment of the present invention provides a method for reducing dried damage of an ophthalmic mucosa cell, including a step of allowing, to contact with the ophthalmic mucosa, an aqueous composition for ophthalmological use containing (A) a petrolatum and two or more (B) nonionic surfactants.

The aqueous composition for ophthalmological use can reduce dried damage of an ophthalmic mucosa cell, such as corneal epithelial cell, and therefore is useful also for dry eye (dry condition of the eyes). Thus, one embodiment of the present invention provides an agent for preventing, curing, ameliorating, or reducing a dry eye symptom, containing an aqueous composition for ophthalmological use that contains (A) a petrolatum and two or more (B) nonionic surfactants. Another embodiment of the present invention provides use of (A) a petrolatum and two or more (B) nonionic surfactants in preparing an aqueous composition for ophthalmological use for use in preventing, curing, ameliorating, or reducing a dry eye symptom. Still another embodiment of the present invention provides a method for imparting an effect of preventing, curing, ameliorating, or reducing a dry eye symptom to an aqueous composition for ophthalmological use, including preparing an aqueous composition for ophthalmological use containing (A) a petrolatum and two or more (B) nonionic surfactants. Further, still another embodiment of the present invention provides a method for preventing, curing, ameliorating, or reducing a dry eye symptom, including allowing, to contact with an ophthalmic mucosa, an aqueous composition for ophthalmological use containing (A) a petrolatum and two or more (B) nonionic surfactants.

The component (A) and components (B) and the contents etc. thereof, the other components and the contents etc. thereof, the form of preparation and the application of the aqueous composition, etc. in each of the embodiments described above are as described in the section [1. Aqueous composition for ophthalmological or otolaryngological use].

[4. Aqueous Composition for Otolaryngological Use Contained in a Container Having a Nozzle]

The aqueous composition for otolaryngological use may be contained in a container having a nozzle. In this embodiment, the aqueous composition for otolaryngological use needs only to contain (A) a petrolatum, and preferably further contains one or more (B) nonionic surfactants, and more preferably two or more (B) nonionic surfactants.

The container that contains the aqueous composition for otolaryngological use may be of various types such as a dropping type, an application type, and a spray type depending on the form of the nozzle portion. Those of spray types include a hand-pumping nasal drop container having a mechanism for spraying the aqueous composition by manual operation of a pump provided with the container, and an aerosol type nasal drop container having a mechanism for automatically spraying the aqueous composition by operating a valve provided with the container after filling the container with a propellant such as a compressed gas (e.g., air, oxygen, nitrogen, carbon dioxide, and mixed gas). In view of higher achievement of the allergenic substance removal effect, dry stress related-cell damage reduction/prevention effect, and irritation-relieving or reducing effect upon application, a spray type is preferred, and a hand-pumping type is more preferred.

Thus, one embodiment of the present invention provides an agent for relieving or reducing irritation upon application, containing an aqueous composition for otolaryngological use that contains (A) a petrolatum, and being contained in a container having a spray nozzle. Another embodiment of the present invention provides use of (A) a petrolatum in preparing an aqueous composition for otolaryngological use for relieving or reducing irritation upon application, contained in a container having a spray nozzle. Still another embodiment of the present invention provides a method for imparting an effect of relieving or reducing irritation upon application to an aqueous composition for otolaryngological use, including preparing an aqueous composition for otolaryngological use containing (A) a petrolatum, and being contained in a container having a spray nozzle. Further, still another embodiment of the present invention provides a method for relieving or reducing irritation when an aqueous composition is applied to a nasal cavity mucosa or to an ear, including using (A) a petrolatum in the aqueous composition. This method may further include a step of containing the aqueous composition in a container having a spray nozzle.

The aqueous composition for ophthalmological or otolaryngological use according to this embodiment has an effect of reducing/preventing cell damage due to dry stress (dried damage). Thus, one embodiment of the present invention provides an agent for reducing dry air-related damage of a nasal mucosa cell, containing an aqueous composition for otolaryngological use that contains (A) a petrolatum and two or more (B) nonionic surfactants. Another embodiment of the present invention provides use of (A) a petrolatum and two or more (B) nonionic surfactants in preparing an aqueous composition for otolaryngological use for reducing dried damage of a nasal mucosa cell. Still another embodiment of the present invention provides a method for imparting an effect of reducing dried damage of a nasal mucosa cell to an aqueous composition for otolaryngological use, including preparing an aqueous composition for otolaryngological use containing (A) a petrolatum and two or more (B) nonionic surfactants. Further, still another embodiment of the present invention provides a method for reducing dried damage of a nasal mucosa cell, including a step of allowing, to contact with a nasal mucosa, an aqueous composition for otolaryngological use containing (A) a petrolatum and two or more (B) nonionic surfactants.

The component (A) and components (B) and the contents etc. thereof, and the other components and the contents etc. thereof in each of the embodiments described above are as described in the section [1. Aqueous composition for ophthalmological or otolaryngological use].

EXAMPLES

The present invention will be described below with reference to Test Examples. It is to be understood that the present invention is not limited to Test Examples.

Test Example 1

Pollen Wash-Out Test

Aqueous compositions having the compositions shown in Table 1 were prepared. The oily component and the surfactants were first stirred with a stirrer in a heated condition to a temperature of 60° C., and purified water heated to 60° C. was then added to this mixture, followed by stirring to mix. This mixture was left to cool to room temperature, after which the other components were blended with the mixture, and allowed to dissolve. Then, after adjustment of the pH, purified water was further added to dilute the mixture to a predetermined volume. The white petrolatum used was Sunwhite P200 produced by Nikko Rica Corporation.

Human corneal epithelial cell line HCE-T (RIKEN BioResource Center, No. RCB1384) was seeded in a culture plate (24 wells, manufactured by Corning Japan), and was cultured to confluence under conditions of 37° C., 5% $CO_2$, and a relative humidity of 90%. The cell culture medium used was prepared by adding FCS (produced by DS Pharma Co., Ltd.), DMSO (produced by Wako Pure Chemical Industries, Ltd.), recombinant human EGF (produced by R & D), and insulin solution human (produced by SIGMA), to DMEM/F12 (produced by INVITROGEN) so that the contents thereof would be 5%, 0.5%, 10 ng/mL, and 5 μg/mL, respectively.

The cell culture medium was removed from each well by aspiration, and a cell culture medium of an amount of 0.5 mL having 0.2 mg/mL of *artemisia* pollen (supplied by SIGMA, Cat. P9395-1G) suspended therein was added to each well. Thereafter, each well was incubated under conditions of 37° C. and 5% $CO_2$ for 4 hours to allow the pollen to adsorb to the cells.

Supernatant was removed from each well by aspiration. Then, 500 μL of the aqueous compositions having the composition shown in Table 1 (Examples 1 to 3 and Comparative Example 1) were respectively added to the wells, and the wells were shaken at a rate of 400 revolutions per minute for 30 seconds. After the aqueous composition was removed from each well by aspiration, five arbitrary microscopic images were captured for each well, and the total areas of the remaining pollen were determined using image analysis software (WinROOF).

An average value (4 wells) of the determined total areas of the remaining pollen was calculated for each of the aqueous compositions. The ratio of the total area of the remaining pollen in each of Examples relative to the total area of the remaining pollen of Comparative Example 1 is shown as a pollen remaining amount (%) in Table 1.

TABLE 1

| Unit (% w/v) | Comparative Example 1 | Example 1 | Example 2 | Example 3 |
| --- | --- | --- | --- | --- |
| White petrolatum | — | 0.01 | 0.01 | 0.03 |
| Sesame oil | — | — | 0.05 | 0.05 |

TABLE 1-continued

| Unit (% w/v) | Comparative Example 1 | Example 1 | Example 2 | Example 3 |
| --- | --- | --- | --- | --- |
| Polysorbate 80 (HLB 15) | 0.2 | 0.2 | 0.2 | 0.2 |
| Polyoxyethylene castor oil 3 (HLB 3) | 0.2 | 0.2 | 0.2 | 0.2 |
| Sodium chloride | 0.6 | 0.6 | 0.6 | 0.6 |
| Boric acid | 1.2 | 1.2 | 1.2 | 1.2 |
| Borax | 0.2 | 0.2 | 0.2 | 0.2 |
| Purified water | Balance | Balance | Balance | Balance |
| pH | 7.25 | 7.26 | 7.28 | 7.26 |
| Pollen remaining amount (%) | — | 90.6 | 43.0 | 24.1 |

Comparing with the aqueous composition containing only two surfactants, the aqueous compositions further containing white petrolatum showed, surprisingly, a tendency of a smaller remaining amount of the pollen remaining on corneal epithelial cells. It has also been demonstrated that the aqueous compositions further containing sesame oil each exhibit a significant decrease in the remaining amount of the pollen, and that therefore the pollen wash-out effect improves.

Reference Test Example 1

Solubilization Test (1)

Aqueous compositions having the compositions shown in Table 2 were prepared. Either white petrolatum or liquid paraffin and polysorbate 80 were first stirred with a stirrer in a heated condition to a temperature of 60° C., and purified water heated to 60° C. was then added to this mixture, followed by stirring to mix. This mixture was left to cool to room temperature, after which purified water was further added to dilute the mixture to a predetermined volume.

The aqueous compositions in Reference Examples 1 and 2 were visually evaluated immediately after the preparation in terms of the occurrence or non-occurrence of oil layer separation according to the following criteria. The results are shown in Table 2 and FIG. 1.

<Criteria to Determine Occurrence or Non-Occurrence of Oil Layer Separation>

Excellent: No separation occurs between oil and aqueous layers even under stationary conditions.

Good: Oil and aqueous layers separate from each other under stationary conditions, but mix together homogeneously by inversion.

Not Good: Oil and aqueous layers separate from each other. No mixture occurs even with inversion.

TABLE 2

| Unit (% w/v) | Reference Example 1 | Reference Example 2 |
| --- | --- | --- |
| White petrolatum | — | 0.01 |
| Liquid paraffin | 0.01 | — |
| Polysorbate 80 (HLB 15) | 0.5 | 0.5 |
| Purified water | Balance | Balance |
| Oil layer separation | Excellent | Not Good |

Both petrolatum and liquid paraffin are known as non-polar oils, and are used to produce eye drops, which are already distributed in the market. As shown in Table 2, the aqueous composition containing liquid paraffin exhibits no separation of an oil layer, and is clear, if polysorbate 80 is used as the surfactant. In contrast, the aqueous composition containing white petrolatum has been proven to be very poorly soluble with the addition of only polysorbate 80. In other words, even though white petrolatum and liquid paraffin are both non-polar oils, it has been demonstrated that white petrolatum has a problem that liquid paraffin does not have in terms of solubilization.

Test Example 2

Test on Solubilization

Aqueous compositions having the compositions shown in Tables 3 and 4 were prepared. The oily component and the surfactants were stirred with a stirrer in a heated condition to a temperature of 60° C., and purified water heated to 60° C. was then added to this mixture, followed by stirring to mix. This mixture was left to cool to room temperature, after which the other components were blended with the mixture, and allowed to dissolve. Then, after adjustment of the pH, purified water was further added to dilute the mixture to a predetermined volume. The white petrolatum used was Sunwhite P200 produced by Nikko Rica Corporation.

The aqueous compositions (Examples 4 to 11) were evaluated in terms of the occurrence or non-occurrence of oil layer separation in a similar manner to Reference Test Example 1. The light transmittance at a wavelength of 660 nm of each of these aqueous compositions one day after the preparation was also determined using a spectrophotometer (UV-VIS Spectrophotometer UV-2450, manufactured by Shimadzu Corporation). This light transmittance serves as an index of clarity of an aqueous composition. The results are shown also in Tables 3 and 4.

TABLE 3

| Unit (% w/v) | Example 4 | Example 5 | Example 6 | Example 7 |
|---|---|---|---|---|
| White petrolatum | 0.01 | 0.01 | 0.01 | 0.01 |
| Polysorbate 80 (HLB 15) | 0.2 | 0.2 | 0.3 | 0.3 |
| Polyoxyethylene castor oil 3 (HLB 3) | 0.2 | 0.2 | — | — |
| Polyoxyethylene castor oil 10 (HLB 6.5) | — | — | 0.1 | 0.1 |
| Sesame oil | 0.05 | 0.05 | 0.05 | — |
| Tocopherol acetate | — | — | — | 0.05 |
| Boric acid | — | 1.2 | — | — |
| Borax | — | 0.2 | — | — |
| Purified water | Balance | Balance | Balance | Balance |
| pH | 8.1 | 7.2 | 6.9 | 6.7 |
| Oil layer separation | Excellent | Excellent | Excellent | Excellent |
| Transmittance (% T: 660 nm) | 91.3 | 95 | 96.1 | 91.1 |

TABLE 4

| Unit (% w/v) | Example 8 | Example 9 | Example 10 | Example 11 |
|---|---|---|---|---|
| White petrolatum | 0.01 | 0.01 | 0.01 | 0.01 |
| Polyoxyethylene hydrogenated castor oil 60 (HLB 14.0) | 0.2 | 0.1 | 0.3 | 0.2 |
| Polyoxyethylene castor oil 3 (HLB 3) | 0.2 | — | 0.1 | — |
| Polyoxyethylene castor oil 10 (HLB 6.5) | — | 0.3 | — | 0.2 |
| Sesame oil | 0.05 | 0.05 | 0.05 | 0.05 |
| Purified water | Balance | Balance | Balance | Balance |
| pH | 8.2 | 8.0 | 8.3 | 8.2 |
| Oil layer separation | Excellent | Excellent | Excellent | Excellent |
| Transmittance (% T: 660 nm) | 75.6 | 25.6 | 52.7 | 29.6 |

As shown in Table 3, inclusion of polyoxyethylene castor oil 3 or polyoxyethylene castor oil 10 in addition to polysorbate 80 permits preparation of clear aqueous compositions without oil layer separation. Comparison between the results of Examples 4 and 5 shows that further inclusion of a boric acid buffer permits preparation of an aqueous composition having higher clarity. As shown in Table 4, when polyoxyethylene castor oil 60 is used instead of polysorbate 80, inclusion of polyoxyethylene castor oil 3 or polyoxyethylene castor oil 10 also permits preparation of an aqueous composition without oil layer separation.

Test Example 3

Cell Drying Test

Aqueous compositions having the compositions shown in Table 5 were prepared. The oily component and the surfactants were stirred with a stirrer in a heated condition to a temperature of 60° C., and purified water heated to 60° C. was then added to this mixture, followed by stirring to mix. This mixture was left to cool to room temperature, after which the other components were blended with the mixture, and allowed to dissolve. Then, after adjustment of the pH, purified water was further added to dilute the mixture to a predetermined volume. The white petrolatum used was Sunwhite P200 produced by Nikko Rica Corporation, and the yellow petrolatum used was Penreco 4650 produced by Penreco.

TABLE 5

| Unit (% w/v) | Comparative Example 2 | Example 12 | Example 13 |
|---|---|---|---|
| Yellow petrolatum | — | 0.01 | — |
| White petrolatum | — | — | 0.01 |
| Sesame oil | 0.05 | 0.05 | 0.05 |
| Polysorbate 80 (HLB 15) | 0.3 | 0.3 | 0.3 |
| Polyoxyethylene castor oil 3 (HLB 3) | 0.15 | 0.15 | 0.15 |
| Polyoxyl 140 stearate (HLB 17.5) | 0.1 | 0.1 | 0.1 |
| Sodium chloride | 0.6 | 0.6 | 0.6 |
| Boric acid | 1.2 | 1.2 | 1.2 |
| Borax | 0.2 | 0.2 | 0.2 |
| Purified water | Balance | Balance | Balance |
| pH | 7.2 | 7.2 | 7.2 |

Human corneal epithelial cell line HCE-T (RIKEN BioResource Center, No. RCB1384) was seeded in a culture plate (96 wells, manufactured by Corning Japan), and was cultured to confluence under conditions of 37° C., 5% $CO_2$, and a relative humidity of 90%. The cell culture medium used was prepared by adding FCS (produced by DS Pharma Co., Ltd.), DMSO (produced by Wako Pure Chemical Industries, Ltd.), recombinant human EGF (produced by R & D), and insulin solution human (produced by SIGMA), to DMEM/F12 (produced by INVITROGEN) so that the contents thereof would be 5%, 0.5%, 10 ng/mL, and 5 μg/mL, respectively.

The cell culture medium was removed from each well by aspiration, and 50 μL of the aqueous compositions (Examples 12 to 13 and Comparative Example 2) having the compositions shown in Table 5 were added to appropriate wells. Thereafter, each well was incubated under conditions of 37° C. and 5% $CO_2$ for 15 minutes. After the aqueous composition was removed from each well by aspiration, dry stress was applied by leaving the samples in a clean bench for 20 minutes, after which the numbers of viable cells were determined. The numbers of viable cells were determined by adding a reagent for determining the number of cells called Cell Counting Kit-8 (produced by Dojindo) to each well, incubating the samples at 37° C. and 5% $CO_2$ for one hour, and measuring the absorbance at a wavelength of 450 nm. Cell viabilities were each determined using the number of viable cells determined and that of a blank sample processed in a similar manner to the foregoing description except that no dry stress was applied. The results are shown in FIG. 2.

Figure 2:
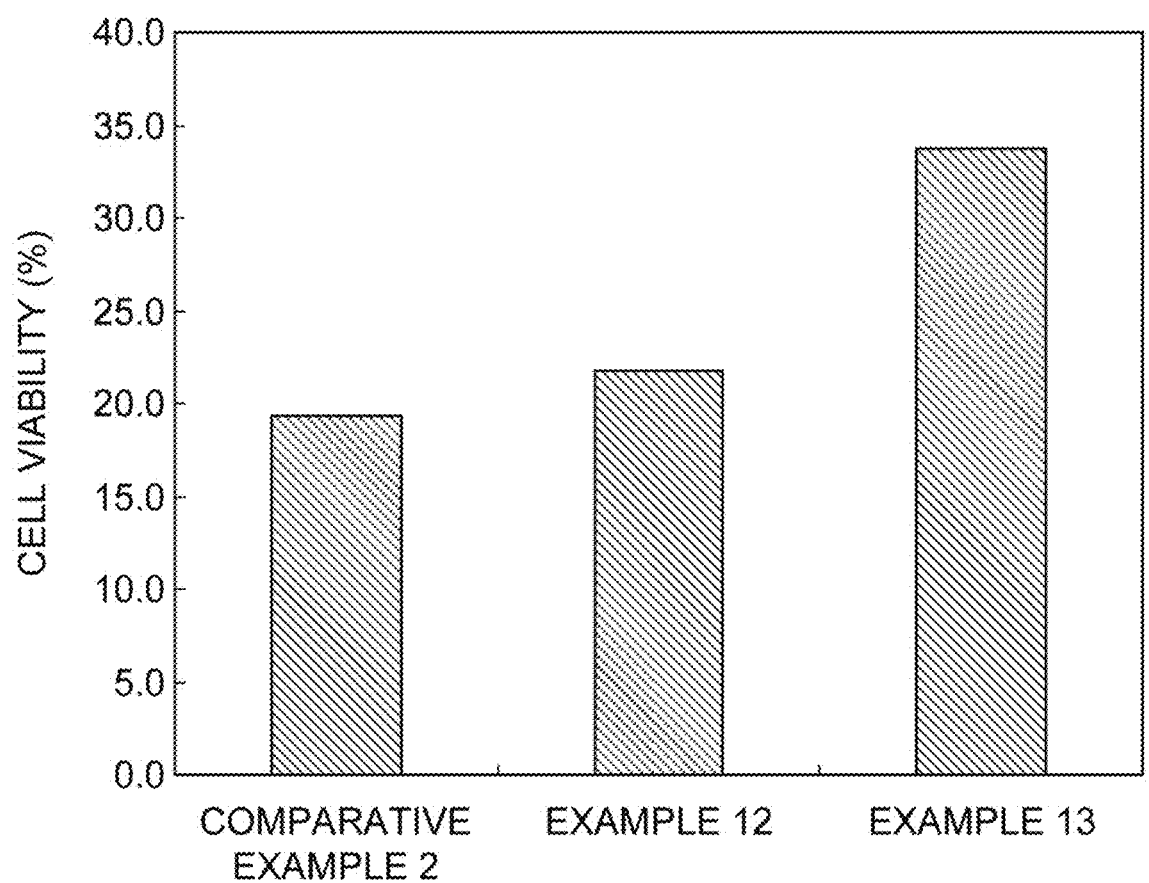
FIG. 2 is a graph illustrating cell viabilities in Test Example 3.

As shown in FIG. 2, it has been demonstrated that further inclusion of petrolatum in the aqueous composition of Comparative Example 2 permits cell necrosis due to dry stress to be significantly reduced or prevented. It has also been demonstrated that, among petrolatums, the use of white petrolatum can further reduce or prevent cell necrosis due to dry stress than the use of yellow petrolatum.

Test Example 4

Evaluation of Usability

Aqueous compositions having the compositions shown in Table 6 were prepared. The oily component and the surfactants were stirred with a stirrer in a heated condition to a temperature of 60° C., and purified water heated to 60° C. was then added to this mixture, followed by stirring to mix. This mixture was left to cool to room temperature, after which the other components were blended with the mixture, and allowed to dissolve. Then, after adjustment of the pH, purified water was further added to dilute the mixture to a predetermined volume. The white petrolatum used was Sunwhite P200 produced by Nikko Rica Corporation. Each of these aqueous compositions prepared was charged in a metered-dose nasal spray container (of a manual operation type). The viscosity of each of these aqueous compositions was determined according to the test method "Cone-flat plate-type rotational viscometer (Cone-plate type viscometer)" described in Method II Viscosity measurement by rotational viscometer, Viscosity Determination, General Tests of Japanese Pharmacopoeia, 16th revision. The test conditions were as follows.
  Measurement temperature: 25° C.
  Measurement device: TV-20 (manufactured by Told Sangyo Co., Ltd.)
  Rotational speed: 50 rpm
  Rotor: Standard cone rotor (1° 34'×R24)
  Set time: Viscosity after 3 minutes
The aqueous composition of Example 14 was evaluated in terms of the occurrence or non-occurrence of oil layer separation in a similar manner to Reference Test Example 1, and in terms of the light transmittance at a wavelength of 660 nm in a similar manner to Test Example 2.

TABLE 6

| Unit (% w/v) | Comparative Example 3 | Example 14 |
| --- | --- | --- |
| Propylene glycol | 20 | 20 |
| Polysorbate 80 (HLB 15) | 0.2 | 0.2 |
| Polyoxyethylene castor oil 3 (HLB 3) | 0.2 | 0.2 |
| White petrolatum | — | 0.01 |
| Sesame oil | 0.05 | 0.05 |
| Polyethylene glycol 4000 | 15 | 15 |
| Anhydrous citric acid | 0.01 | 0.01 |
| Sodium citrate dihydrate | 0.001 | 0.001 |
| Disodium edetate hydrate | 0.1 | 0.1 |
| Benzalkonium chloride solution | 0.1 | 0.1 |
| Purified water | Balance | Balance |

TABLE 6-continued

| Unit (% w/v) | Comparative Example 3 | Example 14 |
| --- | --- | --- |
| pH | 6.5 | 6.5 |
| Viscosity (mPa · s) | 10.7 | 10.8 |
| Oil layer separation | — | Excellent |
| Transmittance (% T: 660 nm) | — | 95.7 |
| Score average | 45.6 | 12.0 |

A test for evaluate irritating sensation caused by the aqueous compositions was conducted on five subjects who are in good condition in their nasal cavity mucosae, using visual analog scale (VAS) scores. Specifically, the nasal drops of Comparative Example 3 and Example 14 were applied by administering two pushes thereof into each nostril, and irritating sensation was evaluated immediately after the administration. The evaluation was conducted as follows. Each of the subjects puts a mark depending on the degree of irritating sensation on the subjective symptom research sheet having a line marked at a position of 100 mm, in such a manner that a mark on 0 mm means that no irritation was sensed, while a mark on 100 mm means that a high incidence of irritation was sensed. This length (mm) was measured as a score of the subjective symptom, and the averages for the five subjects were calculated.

The results are shown also in Table 6. It has been demonstrated that inclusion of petrolatum in the aqueous composition relieves smarting upon administration. Thus, it has been demonstrated that inclusion of petrolatum in an aqueous composition for otolaryngological use charged in a spray-type container relieves irritating sensation (smarting), and thus can provide a preparation that is comfortably administered.

Test Example 5

Test on Solubilization

Aqueous compositions having the compositions shown in Tables 7 and 8 were prepared. The oily component and the surfactants were stirred with a stirrer in a heated condition to a temperature of 60° C., and purified water heated to 60° C. was then added to this mixture, followed by stirring to mix. This mixture was left to cool to room temperature, after which the other components were blended with the mixture, and allowed to dissolve. Then, after adjustment of the pH, purified water was further added to dilute the mixture to a predetermined volume. The white petrolatum used was Sunwhite P200 produced by Nikko Rica Corporation.

The aqueous compositions (Examples 15 to 27) were evaluated in terms of the occurrence or non-occurrence of oil layer separation n a similar manner to Reference Test Example 1. The light transmittance at a wavelength of 660 nm of each of these aqueous compositions one day after the preparation was also determined using a spectrophotometer (UV-VIS Spectrophotometer UV-2450, manufactured by Shimadzu Corporation). This light transmittance serves as an index of clarity of an aqueous composition. The results are shown also in Tables 7 and 8.

TABLE 7

| | Unit (% w/v) | | | | | |
|---|---|---|---|---|---|---|
| | Example 15 | Example 16 | Example 17 | Example 18 | Example 19 | Example 20 |
| White petrolatum | 0.1 | 0.001 | 0.01 | 0.01 | 0.01 | 0.01 |
| Polysorbate 80 (HLB 15) | 2 | 0.2 | 0.2 | — | — | — |
| Polyoxyethylene hydrogenated castor oil 60 (HLB 14.0) | — | — | — | 0.2 | 0.2 | 0.2 |
| Polyoxyethylene castor oil 3 (HLB 3) | 2 | 0.2 | 0.2 | 0.2 | 0.2 | 0.2 |
| Sesame oil | 0.5 | 0.05 | — | 0.05 | 0.05 | 0.05 |
| Castor oil | — | — | 0.05 | — | — | — |
| Sodium chondroitin sulfate | — | — | — | 0.5 | — | — |
| Sodium hyaluronate | — | — | — | — | 0.01 | — |
| Hydroxypropyl methyl cellulose | — | — | — | — | — | 0.1 |
| l-Menthol | 0.005 | 0.005 | 0.005 | 0.005 | 0.005 | 0.005 |
| Boric acid | 1.2 | 1.2 | 1.2 | 1.2 | 1.2 | 1.2 |
| Borax | 0.2 | 0.2 | 0.2 | 0.01 | 0.01 | 0.01 |
| Purified water | Balance | Balance | Balance | Balance | Balance | Balance |
| pH | 7.2 | 7.2 | 7.2 | 6.0 | 6.0 | 6.0 |
| Viscosity (mPa·s) | 1.25 | 1.02 | 1.02 | 1.61 | 2.6 | 2.14 |
| Oil layer separation | Excellent | Excellent | Excellent | Excellent | Excellent | Excellent |
| Transmittance (% T: 660 nm) | 65.4 | 92.9 | 38.4 | 93.6 | 93.6 | 93.6 |

TABLE 8

| | Unit (% w/v) | | | | | | |
|---|---|---|---|---|---|---|---|
| | Example 21 | Example 22 | Example 23 | Example 24 | Example 25 | Example 26 | Example 27 |
| White petrolatum | 0.01 | 0.1 | 0.001 | 0.01 | 0.01 | 0.01 | 0.01 |
| Polysorbate 80 (HLB 15) | 0.2 | 2 | 0.2 | 0.2 | — | — | — |
| Polyoxyethylene hydrogenated castor oil 60 (HLB 14.0) | — | — | — | — | 0.2 | 0.2 | 0.2 |
| Polyoxyethylene castor oil 3 (HLB 3) | 0.2 | 2 | 0.2 | 0.2 | 0.2 | 0.2 | 0.2 |
| Sesame oil | 0.05 | 0.5 | 0.05 | — | 0.05 | 0.05 | 0.05 |
| Castor oil | — | — | — | 0.05 | — | — | — |
| Sodium chondroitin sulfate | — | — | — | — | 0.5 | — | — |
| Sodium hyaluronate | — | — | — | — | — | 0.01 | — |
| Hydroxypropyl methyl cellulose | — | — | — | — | — | — | 0.1 |
| Disodium hydrogen phosphate | 1 | 1 | 1 | 1 | 0.8 | 0.8 | 0.8 |
| Sodium dihydrogen phosphate | 0.2 | 0.2 | 0.2 | 0.2 | 1.8 | 1.8 | 1.8 |
| Purified water | Balance | Balance | Balance | Balance | Balance | Balance | Balance |
| pH | 7.2 | 7.2 | 7.2 | 7.2 | 6.0 | 6.0 | 6.0 |
| Viscosity (mPa·s) | 1.04 | 1.24 | 1.04 | 1.04 | 1.38 | 2.36 | 2.19 |
| Oil layer separation | Excellent | Excellent | Excellent | Excellent | Excellent | Excellent | Excellent |
| Transmittance (% T: 660 nm) | 92.6 | 65.7 | 87.7 | 25.2 | 91.3 | 91.3 | 91.3 |

Preparation Examples

Eye drops (including those applicable during wear of contact lenses), eye washes, multi-purpose solutions (MPSs), solutions for wearing contact lenses, and nasal drops were prepared according to the formulations provided in Tables 9 to 11. All values in these tables are given in units of % w/v.

TABLE 9

| | Preparation Example 1 Eye drop | Preparation Example 2 Eye drop | Preparation Example 3 Eye drop | Preparation Example 4 Eye drop | Preparation Example 5 Eye drop |
|---|---|---|---|---|---|
| White petrolatum | 0.01 | 0.1 | 0.5 | — | 0.01 |
| Yellow petrolatum | — | — | — | 0.001 | — |
| Polyoxyethylene (20) sorbitan monooleate ester | 0.15 | 1 | 6 | — | 0.2 |
| Polyoxyethylene hydrogenated castor oil 60 | — | 1 | — | — | — |
| Polyoxyethylene hydrogenated castor oil 40 | — | — | — | 0.01 | — |

TABLE 9-continued

| | Preparation Example 1 Eye drop | Preparation Example 2 Eye drop | Preparation Example 3 Eye drop | Preparation Example 4 Eye drop | Preparation Example 5 Eye drop |
|---|---|---|---|---|---|
| Polyoxyethylene hydrogenated castor oil 100 | — | — | — | — | — |
| Polyoxyethylene castor oil 3 | 0.1 | — | 6 | — | 0.2 |
| Polyoxyethylene castor oil 10 | — | 1 | — | 0.005 | — |
| Polyoxyethylene (196)-polyoxypropylene (67) block copolymer | — | — | 0.1 | 0.5 | — |
| Polyethylene glycol monostearate 40 | 0.01 | — | — | — | — |
| Sesame oil | 0.05 | 1 | 1 | 0.005 | 0.05 |
| Castor oil | — | — | 1 | — | — |
| Tetrahydrozoline hydrochloride | 0.01 | — | — | — | 0.005 |
| Naphazoline hydrochloride | — | — | — | — | — |
| Epinephrine hydrochloride | — | — | — | — | — |
| Phenylephrine hydrochloride | — | — | — | — | — |
| Neostigmine methylsulfate | — | — | — | — | — |
| Pranoprofen | — | — | — | — | — |
| Sodium cromoglicate | — | 1 | — | — | — |
| Sodium azulene sulfonate | — | — | 0.5 | — | — |
| Dipotassium glycyrrhizate | — | — | — | 0.001 | — |
| Zinc sulfate | — | — | — | — | — |
| Berberine sulfate | — | — | — | — | — |
| Chlorpheniramine maleate | 0.03 | 0.02 | 0.002 | — | — |
| Pyridoxine hydrochloride | 0.1 | 0.05 | — | — | — |
| d-α-Tocopherol acetate | — | 0.5 | — | — | 0.05 |
| Retinol palmitate | — | — | 60000 units | — | — |
| Potassium aspartate | — | — | — | 1.2 | — |
| Aminoethyl sulfonic acid | — | — | 1 | — | — |
| Sodium chondroitin sulfate | 0.5 | 0.2 | — | — | — |
| Polyvinyl pyrrolidone K25 | — | — | — | — | — |
| Hydroxyethyl cellulose | — | — | 0.005 | — | — |
| Hydroxypropyl methyl cellulose | — | — | — | 0.005 | — |
| l-Menthol | 0.005 | 0.01 | 0.05 | 0.0001 | — |
| d-Camphor | — | 0.005 | — | — | — |
| dl-Camphor | — | — | — | — | — |
| d-Borneol | — | 0.002 | — | — | — |
| Geraniol | — | — | 0.005 | — | — |
| Eucalyptus oil | — | — | — | 0.005 | — |
| Cool mint oil | — | — | 0.005 | — | — |
| Boric acid | 2 | 0.5 | — | — | — |
| Borax | Appropriate amount | Appropriate amount | — | — | — |
| Sodium dihydrogen phosphate dihydrate | — | — | 1 | — | 2 |
| Disodium hydrogen phosphate dodecahydrate | — | — | Appropriate amount | — | Appropriate amount |
| Sodium citrate dihydrate | — | — | — | Appropriate amount | — |
| Anhydrous citric acid | — | — | — | 1 | — |
| Sodium chloride | — | 0.5 | — | — | — |
| Sodium edetate | 0.01 | 0.01 | 0.1 | 0.001 | 0.001 |
| Dibutylhydroxytoluene | 0.005 | 0.001 | .0001 | 0.001 | 0.1 |
| Hydrochloric acid | Appropriate amount | Appropriate amount | Appropriate amount | Appropriate amount | Appropriate amount |
| Sodium hydroxide | Appropriate amount | Appropriate amount | Appropriate amount | Appropriate amount | Appropriate amount |
| Purified water | Appropriate amount | Appropriate amount | Appropriate amount | Appropriate amount | Appropriate amount |
| pH | 7 | 5.5 | 8 | 4 | 7 |

| | Preparation Example 6 Eye drop | Preparation Example 7 Eye drop | Preparation Example 8 Eye drop | Preparation Example 9 Eye drop | Preparation Example 10 Eye drop |
|---|---|---|---|---|---|
| White petrolatum | 0.1 | 0.5 | — | 0.03 | 0.0001 |
| Yellow petrolatum | — | — | 0.005 | — | — |
| Polyoxyethylene (20) sorbitan monooleate ester | 1 | 6 | — | — | 0.01 |
| Polyoxyethylene hydrogenated castor oil 60 | — | — | — | 0.3 | — |
| Polyoxyethylene hydrogenated castor oil 40 | 1 | — | 0.01 | — | — |
| Polyoxyethylene hydrogenated castor oil 100 | — | — | — | — | — |
| Polyoxyethylene castor oil 3 | — | 6 | — | 0.3 | 0.005 |
| Polyoxyethylene castor oil 10 | 1 | — | 0.005 | — | — |
| Polyoxyethylene (196)-polyoxypropylene (67) block copolymer | — | — | — | — | — |

TABLE 9-continued

| | | | | | |
|---|---|---|---|---|---|
| Polyethylene glycol monostearate 40 | — | — | — | — | — |
| Sesame oil | — | 1 | 1 | 0.05 | 0.03 |
| Castor oil | 1 | 1 | 1 | — | — |
| Tetrahydrozoline hydrochloride | — | — | — | — | — |
| Naphazoline hydrochloride | 0.003 | — | — | — | — |
| Epinephrine hydrochloride | — | 0.0003 | — | — | — |
| Phenylephrine hydrochloride | — | — | 0.01 | — | — |
| Neostigmine methylsulfate | — | — | — | — | — |
| Pranoprofen | — | — | — | 0.05 | 0.05 |
| Sodium cromoglicate | — | — | — | — | 0.5 |
| Sodium azulene sulfonate | — | — | — | — | — |
| Dipotassium glycyrrhizate | — | — | — | — | — |
| Zinc sulfate | — | 0.025 | — | — | — |
| Berberine sulfate | — | — | 0.25 | — | — |
| Chlorpheniramine maleate | — | — | — | 0.03 | 0.03 |
| Pyridoxine hydrochloride | — | — | — | — | — |
| d-α-Tocopherol acetate | — | — | — | — | — |
| Retinol palmitate | 5000 units | — | — | — | — |
| Potassium aspartate | — | 0.01 | 1 | — | — |
| Aminoethyl sulfonic acid | — | 1 | 0.01 | — | — |
| Sodium chondroitin sulfate | — | — | — | 0.5 | 0.5 |
| Polyvinyl pyrrolidone K25 | — | — | — | 3 | — |
| Hydroxyethyl cellulose | — | — | — | — | — |
| Hydroxypropyl methyl cellulose | — | — | — | — | — |
| l-Menthol | — | — | — | 0.01 | 0.005 |
| d-Camphor | — | — | — | — | 0.002 |
| dl-Camphor | — | — | — | — | — |
| d-Borneol | — | — | — | — | — |
| Geraniol | — | — | — | — | — |
| Eucalyptus oil | — | — | — | — | — |
| Cool mint oil | — | — | — | — | — |
| Boric acid | — | 2 | 2 | 1.5 | 1.5 |
| Borax | — | Appropriate amount | Appropriate amount | Appropriate amount | Appropriate amount |
| Sodium dihydrogen phosphate dihydrate | — | — | — | — | — |
| Disodium hydrogen phosphate dodecahydrate | — | — | — | — | — |
| Sodium citrate dihydrate | Appropriate amount | — | — | — | — |
| Anhydrous citric acid | 2 | — | — | — | — |
| Sodium chloride | — | — | — | — | — |
| Sodium edetate | 0.01 | 0.1 | 0.001 | 0.01 | 0.01 |
| Dibutylhydroxytoluene | 0.001 | 0.001 | 0.001 | 0.002 | 0.004 |
| Hydrochloric acid | Appropriate amount | Appropriate amount | Appropriate amount | Appropriate amount | Appropriate amount |
| Sodium hydroxide | Appropriate amount | Appropriate amount | Appropriate amount | Appropriate amount | Appropriate amount |
| Purified water | Appropriate amount | Appropriate amount | Appropriate amount | Appropriate amount | Appropriate amount |
| pH | 6 | 5 | 7.5 | 7 | 6 |

TABLE 10

| | Preparation Example 11 Eye drop | Preparation Example 12 Eye drop | Preparation Example 13 Eye drop | Preparation Example 14 Eye drop | Preparation Example 15 Eye drop |
|---|---|---|---|---|---|
| White petrolatum | 0.01 | — | 0.01 | 0.002 | 0.03 |
| Yellow petrolatum | — | 0.1 | — | — | — |
| Liquid paraffin | — | — | — | 0.5 | — |
| Polyoxyethylene (20) sorbitan monooleate ester | — | 1 | 0.2 | 1 | — |
| Polyoxyethylene hydrogenated castor oil 60 | 0.3 | — | — | — | — |
| Polyoxyethylene hydrogenated castor oil 40 | — | — | — | 2 | — |
| Polyoxyethylene hydrogenated castor oil 100 | — | — | — | — | 0.5 |
| Polyoxyethylene castor oil 3 | — | — | 0.1 | — | — |
| Polyoxyethylene castor oil 10 | 0.2 | 1.2 | — | — | — |
| Polyoxyethylene castor oil 35 | — | — | 0.5 | — | 0.4 |
| Polyoxyethylene castor oil 70 | — | — | — | — | — |
| Polyethylene glycol monostearate 4 | — | — | — | — | — |

TABLE 10-continued

| | | | | | |
|---|---|---|---|---|---|
| Polyethylene glycol monostearate 40 | — | 1 | — | — | — |
| Sesame oil | — | 0.05 | 0.05 | 0.03 | — |
| Castor oil | 0.1 | 0.01 | — | — | 0.05 |
| Tetrahydrozoline hydrochloride | — | — | — | — | — |
| Naphazoline hydrochloride | 0.003 | — | — | — | — |
| Epinephrine hydrochlorid | — | — | — | — | — |
| Phenylephrine hydrochloride | — | — | — | — | — |
| Neostigmine methylsulfate | — | — | — | — | — |
| Pranoprofen | 0.08 | 0.05 | — | — | — |
| Sodium cromoglicate | — | 3 | — | — | — |
| Epsilon-aminocaproic acid | — | — | — | — | — |
| Allantoin | — | — | — | — | — |
| Dipotassium glycyrrhizate | — | — | — | — | — |
| Zinc sulfate | — | — | — | — | — |
| Berberine sulfate | — | — | — | — | — |
| Chlorpheniramine maleate | 0.03 | 0.03 | — | — | — |
| Flavin adenine dinucleotide sodium | — | — | — | — | 0.05 |
| Cyanocobalamin | — | — | — | — | — |
| Pyridoxine hydrochloride | — | — | — | — | — |
| d-α-Tocopherol acetate | — | — | — | — | 0.05 |
| Panthenol | — | — | — | — | — |
| Retinol palmitate | — | — | — | 5000 units | 50000 units |
| Potassium aspartate | — | — | — | — | — |
| Aminoethyl sulfonic acid | — | — | — | — | — |
| Sodium chondroitin sulfate | 1 | 0.05 | 0.5 | 0.5 | 1 |
| Polyvinyl alcohol | — | — | — | 0.1 | — |
| Polyethylene glycol | — | — | — | — | — |
| Methyl cellulose | — | — | — | — | 1 |
| Hydroxyethyl cellulose | — | — | 0.5 | — | — |
| Hydroxypropyl methyl cellulose | — | — | — | 0.5 | — |
| l-Menthol | — | 0.001 | 0.005 | — | — |
| d-Camphor | — | — | — | — | — |
| dl-Camphor | — | 0.001 | — | — | — |
| d-Borneol | — | — | — | — | — |
| Geraniol | — | — | — | — | — |
| Bergamot oil | — | — | 0.001 | — | — |
| Cool mint oil | — | 0.001 | 0.0001 | — | — |
| Sodium hyaluronate | — | — | — | — | 0.1 |
| Boric acid | 2 | 0.5 | 1 | — | 1 |
| Borax | Appropriate amount | Appropriate amount | Appropriate amount | — | Appropriate amount |
| Sodium dihydrogen phosphate dihydrate | — | — | — | 1 | 0.01 |
| Disodium hydrogen phosphate dodecahydrate | — | — | — | Appropriate amount | Appropriate amount |
| Sodium citrate dihydrate | — | — | — | — | — |
| Anhydrous citric acid | — | — | — | — | — |
| Trometamol | — | 0.1 | — | — | — |
| Propylene glycol | — | — | — | 0.1 | — |
| Glycerin | — | — | — | 1 | 0.1 |
| Sodium chloride | — | 0.4 | 0.5 | 0.4 | 0.8 |
| Potassium chloride | — | — | 0.1 | 0.05 | 0.1 |
| Benzalkonium chloride concentrated solution 50 | — | — | — | — | — |
| Chlorobutanol | — | — | — | — | — |
| Sodium edetate | 0.1 | 0.0001 | 0.005 | 0.01 | 0.0001 |
| Dibutylhydroxytoluene | 0.01 | 0.00001 | — | — | — |
| Hydrochloric acid | Appropriate amount | Appropriate amount | Appropriate amount | Appropriate amount | Appropriate amount |
| Sodium hydride | Appropriate amount | Appropriate amount | Appropriate amount | Appropriate amount | Appropriate amount |
| Purified water | Appropriate amount | Appropriate amount | Appropriate amount | Appropriate amount | Appropriate amount |
| pH | 5 | 7.5 | 7 | 6 | 7 |

| | Preparation Example 16 Eye drop | Preparation Example 17 Eye drop | Preparation Example 18 Eye drop | Preparation Example 19 Eye drop | Preparation Example 20 Eye drop |
|---|---|---|---|---|---|
| White petrolatum | 0.001 | 0.01 | — | 0.01 | 0.001 |
| Yellow petrolatum | — | — | 0.01 | — | — |
| Liquid paraffin | — | — | — | — | — |
| Polyoxyethylene (20) sorbitan monooleate ester | — | — | 0.2 | 0.3 | 0.1 |
| Polyoxyethylene hydrogenated castor oil 60 | — | 0.3 | — | 0.3 | 0.2 |
| Polyoxyethylene hydrogenated castor oil 40 | — | — | — | — | — |

TABLE 10-continued

| | | | | | |
|---|---|---|---|---|---|
| Polyoxyethylene hydrogenated castor oil 100 | 0.01 | — | — | — | — |
| Polyoxyethylene castor oil 3 | — | — | — | 0.3 | 0.2 |
| Polyoxyethylene castor oil 10 | — | — | — | — | — |
| Polyoxyethylene castor oil 35 | — | — | — | 0.01 | — |
| Polyoxyethylene castor oil 70 | — | — | 0.5 | — | — |
| Polyethylene glycol monostearate 4 | — | 0.1 | — | — | — |
| Polyethylene glycol monostearate 40 | — | — | — | — | — |
| Sesame oil | 0.1 | 0.05 | 0.03 | 0.03 | 0.1 |
| Castor oil | — | — | — | — | — |
| Tetrahydrozoline hydrochloride | — | 0.05 | — | — | — |
| Naphazoline hydrochloride | — | — | 0.03 | — | — |
| Epinephrine hydrochlorid | — | — | — | 0.003 | — |
| Phenylephrine hydrochloride | — | — | — | — | 0.2 |
| Neostigmine methylsulfate | — | 0.005 | 0.005 | 0.005 | 0.001 |
| Pranoprofen | — | — | — | — | — |
| Sodium cromoglicate | — | — | — | — | — |
| Epsilon-aminocaproic acid | — | — | — | 0.1 | 5 |
| Allantoin | — | 0.1 | 0.1 | — | — |
| Dipotassium glycyrrhizate | — | — | — | 0.1 | 0.1 |
| Zinc sulfate | — | — | — | — | 0.05 |
| Berberine sulfate | — | — | — | 0.025 | — |
| Chlorpheniramine maleate | — | 0.03 | 0.03 | 0.03 | 0.03 |
| Flavin adenine dinucleotide sodium | — | — | — | — | — |
| Cyanocobalamin | — | — | — | — | 0.02 |
| Pyridoxine hydrochloride | — | 0.1 | 0.1 | 0.1 | 0.05 |
| d-α-Tocopherol acetate | 0.001 | — | 0.0001 | 0.05 | 0.01 |
| Panthenol | — | 0.2 | 0.01 | — | — |
| Retinol palmitate | — | — | — | — | — |
| Potassium aspartate | — | — | — | 1 | 0.01 |
| Aminoethyl sulfonic acid | — | — | — | 0.5 | — |
| Sodium chondroitin sulfate | 0.01 | — | 0.5 | 0.1 | 0.5 |
| Polyvinyl alcohol | — | — | — | — | — |
| Polyethylene glycol | — | — | — | — | — |
| Methyl cellulose | 0.01 | 0.3 | — | — | — |
| Hydroxyethyl cellulose | — | — | — | — | — |
| Hydroxypropyl methyl cellulose | — | — | — | — | — |
| l-Menthol | 0.01 | 0.05 | — | 0.01 | — |
| d-Camphor | — | 0.01 | — | — | — |
| dl-Camphor | — | — | — | 0.05 | — |
| d-Borneol | 0.001 | — | — | — | — |
| Geraniol | 0.001 | — | — | — | — |
| Bergamot oil | — | — | — | — | — |
| Cool mint oil | 0.005 | 0.01 | — | — | — |
| Sodium hyaluronate | 0.00001 | — | — | — | — |
| Boric acid | 1 | 1 | 1 | 0.4 | 0.2 |
| Borax | Appropriate amount | Appropriate amount | Appropriate amount | Appropriate amount | Appropriate amount |
| Sodium dihydrogen phosphate dihydrate | — | — | — | — | — |
| Disodium hydrogen phosphate dodecahydrate | — | — | — | — | — |
| Sodium citrate dihydrate | 0.01 | — | — | — | — |
| Anhydrous citric acid | Appropriate amount | — | — | — | — |
| Trometamol | — | — | — | — | 1 |
| Propylene glycol | 1 | — | — | — | — |
| Glycerin | — | — | — | — | — |
| Sodium chloride | 0.001 | — | — | — | — |
| Potassium chloride | 0.6 | — | — | — | — |
| Benzalkonium chloride concentrated solution 50 | — | — | — | 0.15 | — |
| Chlorobutanol | — | 0.1 | — | — | — |
| Sodium edetate | 0.1 | 0.005 | 0.01 | 0.05 | 0.01 |
| Dibutylhydroxytoluene | — | — | — | — | — |
| Hydrochloric acid | Appropriate amount | Appropriate amount | Appropriate amount | Appropriate amount | Appropriate amount |
| Sodium hydride | Appropriate amount | Appropriate amount | Appropriate amount | Appropriate amount | Appropriate amount |
| Purified water | Appropriate amount | Appropriate amount | Appropriate amount | Appropriate amount | Appropriate amount |
| pH | 5 | 6 | 7.3 | 5 | 7.5 |

TABLE 11

| | Preparation Example 21 Eye drop for SCL | Preparation Example 22 Eye drop for SCL | Preparation Example 23 Wearing solution | Preparation Example 24 MPS | Preparation Example 25 MPS |
|---|---|---|---|---|---|
| White petrolatum | 0.0001 | 0.05 | 0.01 | 0.05 | 0.001 |
| Yellow petrolatum | — | — | — | — | — |
| Liquid paraffin | — | — | — | — | — |
| Polyoxyethylene (20) sorbitan monooleate ester | 0.01 | 1.2 | 0.1 | 1 | — |
| Polyoxyethylene hydrogenated castor oil 60 | — | — | 0.1 | — | 0.02 |
| Polyoxyethylene hydrogenated castor oil 40 | 0.01 | — | — | — | — |
| Polyoxyethylene hydrogenated castor oil 100 | — | — | 0.1 | — | — |
| Polyoxyethylene castor oil 3 | — | 0.8 | — | 1 | 0.02 |
| Polyoxyethylene castor oil 10 | — | — | — | — | — |
| Polyoxyethylene castor oil 35 | — | — | 0.1 | — | — |
| Polyoxyethylene castor oil 70 | — | — | 0.01 | — | — |
| Polyoxyethylene (196)-polyoxypropylene (67) block copolymer | — | — | 0.1 | — | — |
| Polyoxyethylene (200)-polyoxypropylene (70) block copolymer | 0.1 | — | — | — | — |
| Polyethylene glycol monostearate 40 | — | — | — | — | — |
| Polyethylene glycol monostearate 140 | — | 1 | — | — | — |
| Sesame oil | 0.001 | 0.03 | 0.03 | 0.03 | 0.03 |
| Castor oil | — | — | — | — | — |
| Fluticasone propionate | — | — | — | — | — |
| Flunisolide | — | — | — | — | — |
| Dipotassium glycyrrhizate | — | — | — | — | — |
| Zinc sulfate | — | — | — | — | — |
| Berberine sulfate | — | — | — | — | — |
| Chlorpheniramine maleate | — | — | — | — | — |
| Cyanocobalamin | — | — | — | — | — |
| Pyridoxine hydrochloride | — | — | — | — | — |
| d-α-Tocopherol acetate | — | — | — | — | — |
| Retinol palmitate | — | — | — | — | — |
| Potassium aspartate | — | — | — | — | — |
| Aminoethyl sulfonic acid | — | — | — | — | — |
| Sodium chondroitin sulfate | 0.5 | 0.5 | 0.5 | 0.5 | 0.5 |
| Polyvinyl alcohol | — | — | — | — | — |
| Polyvinyl pyrrolidone K25 | 2.5 | 0.025 | — | — | — |
| Polyethylene glycol | — | — | — | — | — |
| Hydroxyethyl cellulose | 1 | 0.001 | — | 0.05 | — |
| l-Menthol | — | — | 0.25 | — | — |
| d-Camphor | — | — | — | — | — |
| dl-Camphor | — | — | — | — | — |
| d-Borneol | — | — | — | — | — |
| Geraniol | — | — | — | — | — |
| Eucalyptus oil | — | — | — | — | — |
| Bergamot oil | — | — | — | — | — |
| Cool mint oil | — | — | — | — | — |
| Sodium hyaluronate | — | — | — | — | — |
| Boric acid | 1 | 1 | 1 | 0.8 | 1 |
| Borax | Appropriate amount | Appropriate amount | Appropriate amount | Appropriate amount | Appropriate amount |
| Sodium citrate dihydrate | — | — | — | — | — |
| Anhydrous citric acid | — | — | — | — | — |
| Glucose | 0.001 | — | 0.1 | — | — |
| Propylene glycol | — | — | — | — | — |
| Sodium chloride | 0.5 | 0.1 | 0.5 | 0.8 | — |
| Potassium chloride | 0.1 | 0.5 | 0.1 | 0.2 | — |
| Calcium chloride | 0.001 | 0.001 | — | — | — |
| Sodium hydrogen carbonate | 0.05 | 0.05 | — | — | — |
| Magnesium sulfate | 0.1 | 0.01 | — | — | — |
| Alkyl polyaminoethyl glycine solution | — | — | — | — | — |
| Polyhexamethylene biguanide hydrochloride | 0.0005 | 0.00001 | — | 0.00005 | 0.0001 |
| Benzalkonium chloride concentrated solution 50 | — | — | — | — | — |
| Potassium sorbate | — | — | 0.1 | — | — |
| Chlorobutanol | 0.05 | 0.001 | — | — | — |

TABLE 11-continued

| | | | | | |
|---|---|---|---|---|---|
| Sodium edetate | 0.01 | 0.01 | 0.01 | — | — |
| Hydrochloric acid | Appropriate amount | Appropriate amount | Appropriate amount | Appropriate amount | Appropriate amount |
| Sodium hydride | Appropriate amount | Appropriate amount | Appropriate amount | Appropriate amount | Appropriate amount |
| Purified water | Appropriate amount | Appropriate amount | Appropriate amount | Appropriate amount | Appropriate amount |
| pH | 7.5 | 5.5 | 7 | 7.5 | 5.5 |

| | Preparation Example 26 Eye wash | Preparation Example 27 Eye wash | Preparation Example 28 Nasal drop | Preparation Example 29 Nasal drop | Preparation Example 30 Nasal drop |
|---|---|---|---|---|---|
| White petrolatum | 0.01 | 0.5 | 0.05 | — | 0.01 |
| Yellow petrolatum | — | — | — | 0.01 | — |
| Liquid paraffin | — | 0.001 | — | — | — |
| Polyoxyethylene (20) sorbitan monooleate ester | 0.2 | 6 | 1 | 0.2 | — |
| Polyoxyethylene hydrogenated castor oil 60 | — | — | — | — | 0.2 |
| Polyoxyethylene hydrogenated castor oil 40 | — | — | — | — | — |
| Polyoxyethylene hydrogenated castor oil 100 | — | — | — | — | — |
| Polyoxyethylene castor oil 3 | 0.2 | 6 | 0.2 | — | 0.2 |
| Polyoxyethylene castor oil 10 | — | 0.5 | — | 0.2 | — |
| Polyoxyethylene castor oil 35 | — | — | 0.5 | — | — |
| Polyoxyethylene castor oil 70 | — | 0.5 | — | — | — |
| Polyoxyethylene (196)-polyoxypropylene (67) block copolymer | — | — | — | — | — |
| Polyoxyethylene (200)-polyoxypropylene (70) block copolymer | — | — | — | — | — |
| Polyethylene glycol monostearate 40 | — | — | — | 0.5 | — |
| Polyethylene glycol monostearate 140 | — | — | — | — | — |
| Sesame oil | 0.03 | 0.03 | — | 0.05 | 0.05 |
| Castor oil | — | — | 0.05 | — | — |
| Fluticasone propionate | — | — | — | 0.05 | — |
| Flunisolide | — | — | — | — | 0.025 |
| Dipotassium glycyrrhizate | 0.025 | — | — | — | — |
| Zinc sulfate | 0.01 | — | — | — | — |
| Berberine sulfate | 0.001 | — | — | — | — |
| Chlorpheniramine maleate | 0.003 | 0.0001 | — | — | — |
| Cyanocobalamin | 0.001 | 0.003 | — | — | — |
| Pyridoxine hydrochloride | 0.01 | — | — | — | — |
| d-α-Tocopherol acetate | 0.005 | — | — | — | — |
| Retinol palmitate | 5000 units | — | — | — | — |
| Potassium aspartate | 0.1 | — | — | — | — |
| Aminoethyl sulfonic acid | 0.1 | — | — | — | — |
| Sodium chondroitin sulfate | 0.05 | 0.5 | — | 0.5 | — |
| Polyvinyl alcohol | — | — | — | 5 | — |
| Polyvinyl pyrrolidone K25 | — | — | — | — | — |
| Polyethylene glycol | — | — | 20 | 5 | 10 |
| Hydroxyethyl cellulose | 0.5 | — | — | 0.1 | — |
| l-Menthol | 0.05 | — | — | — | — |
| d-Camphor | 0.01 | — | — | — | — |
| dl-Camphor | 0.01 | — | — | — | — |
| d-Borneol | 0.01 | — | — | — | — |
| Geraniol | 0.001 | — | — | — | — |
| Eucalyptus oil | 0.001 | — | — | — | — |
| Bergamot oil | 0.001 | — | — | — | — |
| Cool mint oil | 0.001 | — | — | — | — |
| Sodium hyaluronate | 0.005 | — | — | — | — |
| Boric acid | 2 | 0.5 | — | 1 | — |
| Borax | Appropriate amount | Appropriate amount | — | Appropriate amount | — |
| Sodium citrate dihydrate | — | — | 1 | — | 0.01 |
| Anhydrous citric acid | — | — | Appropriate amount | — | Appropriate amount |
| Glucose | — | — | — | — | — |
| Propylene glycol | — | — | 5 | — | 25 |
| Sodium chloride | — | 0.5 | — | — | — |
| Potassium chloride | — | 0.3 | — | — | — |
| Calcium chloride | — | — | — | — | — |
| Sodium hydrogen carbonate | — | — | — | — | — |
| Magnesium sulfate | — | — | — | — | — |
| Alkyl polyaminoethyl glycine | 0.01 | — | — | — | — |

TABLE 11-continued

| | | | | | |
|---|---|---|---|---|---|
| solution | | | | | |
| Polyhexamethylene biguanide hydrochloride | 0.005 | — | — | — | — |
| Benzalkonium chloride concentrated solution 50 | — | 0.005 | 0.1 | — | 0.1 |
| Potassium sorbate | — | — | — | — | — |
| Chlorobutanol | — | — | — | — | — |
| Sodium edetate | 0.1 | — | — | — | — |
| Hydrochloric acid | Appropriate amount | Appropriate amount | Appropriate amount | Appropriate amount | Appropriate amount |
| Sodium hydride | Appropriate amount | Appropriate amount | Appropriate amount | Appropriate amount | Appropriate amount |
| Purified water | Appropriate amount | Appropriate amount | Appropriate amount | Appropriate amount | Appropriate amount |
| pH | 5.5 | 7.5 | 7.5 | 5.5 | 6 |

The invention claimed is:

1. An aqueous composition formulated for ophthalmological use or otolaryngological use, the aqueous composition comprising:
    (A) white petrolatum that is white;
    two or more (B) nonionic surfactants; and
    C) a fat-soluble vitamin or vegetable oil,
    wherein:
    the component (B) comprises a combination of polysorbate 80 and polyoxyethylene castor oil 3, a combination of polysorbate 80 and polyoxyethylene castor oil 10, a combination of polyoxyethylene hydrogenated castor oil 60 and polyoxyethylene castor oil 3, a combination of polyoxyethylene hydrogenated castor oil 60 and polyoxyethylene castor oil 10, or a combination of polysorbate 80, polyoxyethylene castor oil 3 and polyoxyl 140 stearate,
    the component (C) comprises a sesame oil,
    a total content of (A) the white petrolatum relative to a total amount of the aqueous composition is in a range of from 0.001% to 0.1% w/v,
    a total content of the component (B) relative to a total amount of the aqueous composition is in a range of from 0.4% to 4% w/v, and
    a total content of the component (C) relative to the total amount of the aqueous composition is in a range of from 0.05% to 0.5% w/v.

2. The aqueous composition according to claim 1, further comprising:
    (D) a buffer.

3. The aqueous composition according to claim 1, wherein light transmittance at a wavelength of 660 nm is 60% or higher.

4. A method of treating or reducing an allergic symptom in a subject comprising:
    administering to the subject an effective amount of the aqueous composition of claim 1.

5. A method of treating or reducing a dry eye symptom in a subject comprising:
    administering to the subject an effective amount of the aqueous composition of claim 1.

6. The aqueous composition according to claim 1, further comprising a terpenoid compound.

7. The method according to claim 4, wherein the aqueous composition further contains (D) a buffer.

8. The method according to claim 5, wherein the aqueous composition further contains (D) a buffer.

9. The method according to claim 4, wherein light transmittance of the aqueous composition at a wavelength of 660 nm is 60% or higher.

10. The method according to claim 5, wherein light transmittance of the aqueous composition at a wavelength of 660 nm is 60% or higher.

11. The aqueous composition according to claim 2, wherein the aqueous composition is formulated as an eye drop.

12. The aqueous composition according to claim 1, wherein the white petrolatum is dissolved in the aqueous composition.

* * * * *